United States Patent [19]

Kawatsu

[11] Patent Number: 5,712,052
[45] Date of Patent: Jan. 27, 1998

[54] FUEL CELL GENERATOR AND METHOD OF THE SAME

[75] Inventor: Shigeyuki Kawatsu, Susono, Japan

[73] Assignee: Toyota Jidosha Kabushiki Kaisha, Toyota, Japan

[21] Appl. No.: 552,120

[22] Filed: Nov. 2, 1995

[30] Foreign Application Priority Data

Nov. 2, 1994 [JP] Japan .................. 6-293808
Mar. 31, 1995 [JP] Japan .................. 7-100313
Sep. 22, 1995 [JP] Japan .................. 7-269245

[51] Int. Cl.$^6$ .............. H01M 8/00; H01M 8/04; H01M 8/18
[52] U.S. Cl. .............. 429/13; 429/17; 429/19; 429/22; 429/23; 429/24
[58] Field of Search .............. 429/13, 17, 19, 429/22, 23, 24

[56] References Cited

U.S. PATENT DOCUMENTS

| | | | |
|---|---|---|---|
| 3,615,842 | 10/1971 | Craft, et al. | 136/86 |
| 3,880,722 | 4/1975 | Beltzer | 205/785.5 |
| 4,046,956 | 9/1977 | Fanciullo | 429/20 |
| 4,910,099 | 3/1990 | Gottesfeld | 429/13 |
| 5,456,889 | 10/1995 | Pow et al. | 422/173.1 |

FOREIGN PATENT DOCUMENTS

| | | |
|---|---|---|
| 1305212 | 7/1992 | Canada . |
| 58-133781 | 8/1983 | Japan . |
| 61-109257 | 5/1986 | Japan . |
| 5-205765 | 8/1993 | Japan . |

OTHER PUBLICATIONS

Patent Abstracts of Japan, vol. 14, No. 222 (E-0926), May 10, 1990, JP-A-02-056865, Feb. 26, 1990.
Patent Abstracts of Japan, vol. 8, No. 142 (E-254), Jul. 3, 1984, JP-A-59-051480, Mar. 24, 1984.
Patent Abstracts of Japan, vol. 13, No. 86 (E-720), Feb. 28, 1989, JP-A-63-264875, Nov. 1, 1988.
Patent Abstracts of Japan, vol. 13, No. 31 (E-707), Jan. 24, 1989, JP-A-63-232272, Sep. 28, 1988.

*Primary Examiner*—Kathryn L. Gorgos
*Assistant Examiner*—Edna Wong
*Attorney, Agent, or Firm*—Oblon, Spivak, McClelland, Maier & Neustadt, P.C.

[57] ABSTRACT

The fuel cell generator system of the present invention effectively cancels catalyst poisoning in fuel cells so as to improve the performance of fuel cells. In the fuel cell generator system of the invention, a carbon monoxide sensor is arranged in the middle of a gaseous fuel supply conduit, which connects fuel cells with a reformer for converting methanol and water to a hydrogen-rich gaseous fuel. An electronic control unit of the fuel cell generator system reads the carbon monoxide sensor to input a concentration of carbon monoxide D included in the gaseous fuel (step S250). When the carbon monoxide concentration D obtained is greater than a preset level D0, the electronic control unit increases the air flow fed to a partial oxidizing unit of the reformer (step S270). This accelerates the reaction in the partial oxidizing unit for oxidizing carbon monoxide to carbon dioxide, thereby lowering the concentration of carbon monoxide included in the gaseous fuel.

16 Claims, 16 Drawing Sheets

FUEL CELL GENERATOR AND METHOD OF THE SAME

BACKGROUND OF THE INVENTION

1. Field of the Invention

The present invention relates to a fuel cell generator including a reformer for generating a gaseous fuel and a fuel cell which a supply of the gaseous fuel from the reformer is fed to, and also to a method of the same.

2. Description of the Related Art

Fuel cells are known apparatus in which the chemical energy of a fuel is converted directly into electrical energy. Each fuel cell generally includes a pair of electrodes arranged across an electrolyte, wherein the surface of one electrode is exposed to a reactive hydrogen-rich gaseous fuel while the surface of the other electrode being exposed to an oxidizing gas containing oxygen. The electrical energy is generated between the electrodes through the electrochemical reactions proceeding by the exposure.

In general, the gaseous fuel supplied to such fuel cells is generated by a reformer, which steam-reforms methanol to a hydrogen-rich gaseous fuel. The reformer typically includes a reformer unit for receiving supplies of methanol and water and allowing a reaction of decomposing methanol expressed by Equation (1) given below and a reaction of oxidizing carbon monoxide expressed by Equation (2) given below to proceed simultaneously so as to generate a reformed gas containing hydrogen and carbon dioxide. Equation (3) represents a whole reforming process given as a total of the reactions of Equations (1) and (2). The reformer also includes a shift unit for receiving a supply of the reformed gas from the reformer unit and converting water and non-reacted carbon monoxide included in the reformed gas to hydrogen and carbon dioxide through the oxidizing reaction of Equation (2), thereby generating a hydrogen-rich gaseous fuel.

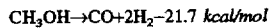  (1)

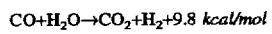  (2)

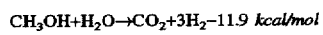  (3)

The rate of reaction of Equation (1) may be different from the rate of reaction of Equation (2), depending upon the reaction conditions, such as temperature and pressure. Carbon monoxide (CO) generated by the reaction of Equation (1) accordingly remains in the gaseous fuel. Carbon monoxide included in the gaseous fuel is adsorbed by platinum catalyst or platinum-containing alloy catalyst on the fuel electrode and interferes with the catalytic action of platinum. This is generally referred to as poisoning of catalyst. The performance of fuel cells is undesirably lowered according to the concentration of carbon monoxide included in the gaseous fuel.

SUMMARY OF THE INVENTION

The object of the present invention is thus to effectively cancel catalyst poisoning in a fuel cell so as to improve the performance of a fuel cell.

The above and the other related objects are realized by a fuel cell generator, which comprises: a reformer for reforming an original fuel to generate a hydrogen-containing gaseous fuel, a fuel cell comprising a pair of electrodes with a catalyst carried thereon, the fuel cell receiving the gaseous fuel fed to the electrodes thereof and generating an electromotive force through an electrochemical reaction of the gaseous fuel, carbon monoxide measurement means for measuring concentration of carbon monoxide included in the gaseous fuel; and reformer operation control means for controlling operation of the reformer according to the concentration of carbon monoxide measured by the carbon monoxide measurement means, thereby decreasing the concentration of carbon monoxide included in the gaseous fuel.

Hereinafter the fuel cell generator thus constructed may be referred to as the fuel cell generator of essential structure. In this structure, the reformer operation control means controls the operation of the reformer according to the concentration of carbon monoxide measured by the carbon monoxide measurement means, thereby decreasing the concentration of carbon monoxide included in the gaseous fuel. An increase in concentration of carbon monoxide included in the gaseous fuel results in poisoning the catalyst carried on the electrodes of the fuel cell. This structure, however, effectively lowers the concentration of carbon monoxide to cancel the catalyst poisoning, thus improving the performance of the fuel cell.

In the fuel cell generator of essential structure, the fuel cell generator further comprises a first flow path for supplying the gaseous fuel to the fuel cell, a second flow path for discharging a residual gas of the gaseous fuel from the fuel cell, and wherein the carbon monoxide measurement means comprises a carbon monoxide sensor disposed in the second flow path.

The primary advantage of this disposition of a carbon monoxide sensor in the second flow path is to allow an increase in concentration of carbon monoxide to be detected at the earlier stage than the disposition of the same carbon monoxide sensor (that is, the carbon monoxide sensor having the same detectable range of carbon monoxide) in the first flow path. The fuel cell generator of this arrangement can accordingly predict occurrence of the catalyst poisoning at its earlier stage, thereby effectively canceling the catalyst poisoning and further improving the performance of the fuel cell.

In the fuel cell generator of essential structure, the fuel cell generator further comprises: a first flow path for supplying the gaseous fuel to the fuel cell, a second flow path for discharging a residual gas of the gaseous fuel from the fuel cell; and wherein the carbon monoxide measurement means comprises: a first carbon monoxide sensor disposed in the first flow path; a second carbon monoxide sensor disposed in the second flow path.

In this alternative structure, the first carbon monoxide sensor and the second carbon monoxide sensor are respectively disposed before and after the fuel cell in the flow path of gaseous fuel. The results of detection with the two carbon monoxide sensors show whether an increase in concentration of carbon monoxide is attributed to an increase in concentration of carbon monoxide included in the gaseous fuel generated by the reformer or to an increase in hydrogen utilization rate in the fuel cell. This structure comprehensively examines an increase in concentration of carbon monoxide and controls the operation of the reformer according to the concentration of carbon monoxide measured by the first and the second carbon monoxide sensors. This results in decreasing the concentration of carbon monoxide included in the gaseous fuel from the reformer without delay, thereby effectively canceling the catalyst poisoning and further improving the performance of a fuel cell.

According to another preferable structure, the carbon monoxide measurement means comprises a first carbon monoxide sensor having a first sensitivity of detection, and a second carbon monoxide sensor having a second sensitivity of detection, which is different from the first sensitivity of detection.

In this preferable structure, the use of two carbon monoxide sensors with different sensitivities of detection favorably widens the detectable range of carbon monoxide. The fuel cell generator of this structure can control the operation of the reformer according to the concentration of carbon monoxide measured by the first and the second carbon monoxide sensors, thereby decreasing the concentration of carbon monoxide included in the gaseous fuel from the reformer without delay.

In the fuel cell generator having the first and the second carbon monoxide sensors with different sensitivities of detection, each of the first carbon monoxide sensor and the second carbon monoxide sensor may comprise: an electrolyte membrane; first and second electrodes with a catalyst carried thereon, the first and second electrodes being arranged across the electrolyte membrane; a gaseous fuel supply conduit for supplying the gaseous fuel to the first electrode; an oxygen gas supply conduit for supplying an oxygen-containing gas to the second electrode; and potential difference detection means for measuring a potential difference between the first and second electrodes while a predetermined load is connected to the first and second electrodes. According to one preferable application, the first carbon monoxide sensor includes platinum as the catalyst, and the second carbon monoxide sensor includes a platinum-containing alloy as the catalyst.

The two carbon monoxide sensors are adjusted to have different sensitivities of detection only by applying different catalysts to the two carbon monoxide sensors, one with a platinum catalyst and the other with a platinum-containing alloy catalyst.

In the fuel cell generator having the first and the second carbon monoxide sensors with different sensitivities of detection, each of the first carbon monoxide sensor and the second carbon monoxide sensor may comprise: an electrolyte membrane; first and second electrodes with a catalyst carried thereon, the first and second electrodes being arranged across the electrolyte membrane; a gaseous fuel supply conduit for supplying the gaseous fuel to the first electrode; an oxygen gas supply conduit for supplying an oxygen-containing gas to the second electrode; and potential difference detection means for measuring a potential difference between the first and second electrodes while a predetermined load is connected to the first and second electrodes. In accordance with one preferable application, either one of the first carbon monoxide sensor and the second carbon monoxide sensor is further provided with temperature control means for controlling temperature of the first electrode.

The sensitivity of detection of carbon monoxide is adjustable in the carbon monoxide sensor with the temperature control means. The two carbon monoxide sensors are controlled to have different sensitivities of detection by applying the temperature control means to one of the carbon monoxide sensors.

In the fuel cell generator of essential structure, the reformer preferably comprises a reformer unit for converting methanol and water to a reformed gas containing hydrogen and carbon dioxide, and a partial oxidizing unit for oxidizing carbon monoxide generated as a by-product of the reformed gas. In this preferable structure, the reformer operation control means is further provided with partial oxidizing unit control means for comparing the concentration of carbon monoxide measured by the carbon monoxide measurement means with a first preset value, and increasing an air flow fed to the partial oxidizing unit when the measured concentration of carbon monoxide is greater than the first preset value.

In this preferable structure, the air flow fed to the partial oxidizing unit of the reformer is increased when the concentration of carbon monoxide measured by the carbon monoxide measurement means is greater than a first preset value. This accelerates the reaction in the partial oxidizing unit for oxidizing carbon monoxide included in the gaseous fuel, thereby reducing the concentration of carbon monoxide. This structure can thus effectively cancel the catalyst poisoning and improve the performance of the fuel cell.

In the fuel cell generator of this structure, the fuel cell generator may further comprise: a first flow path for supplying the gaseous fuel to the fuel cell; and a second flow path for discharging a residual gas of the gaseous fuel from the fuel cell; and wherein the carbon monoxide measurement means comprises: a first carbon monoxide sensor disposed in the first flow path, for generating a first output representing the concentration of carbon monoxide, the first output being compared with the first present value by the partial oxidizing unit control means; and a second carbon monoxide sensor disposed in the second flow path, for generating a second output representing the concentration of carbon monoxide. It is preferable that the fuel cell generator further comprises means for suspending operation of the fuel cell when the first output is greater than the first preset value and the second output is greater than a second preset value, which is greater than the first preset value.

In this preferable structure, the means suspends the operation of the fuel cell, when the concentration of carbon monoxide measured before the fuel cell in the flow path of gaseous fuel is greater than a first preset value and when the concentration of carbon monoxide measured after the fuel cell is greater than a second preset value, which is greater than the first preset value. The two conditions are fulfilled only when the gaseous fuel generated by the reformer includes carbon monoxide of high concentration and the gas utilization rate in the fuel cell is relatively high. Under such conditions, there is no hope of recovery from catalyst poisoning, and the suspended operation of the fuel cell desirably protects the fuel cell and the surrounding elements from significant damages.

In accordance with one preferable application of the invention, the fuel cell generator further comprises: gas utilization calculation means for calculating a degree of utilization of the gaseous fuel in the fuel cell as a gas utilization rate; and gas utilization rate decreasing means for inactivating the reformer operation control means and controlling operation of the reformer to decrease the gas utilization rate when the gas utilization rate is greater than a predetermined level.

In this structure, the gas utilization rate decreasing means inactivates the reformer operation control means and controls operation of the reformer to decrease the gas utilization rate, when the gas utilization rate calculated by the gas utilization rate calculation means is greater than a predetermined level. An increase in concentration of carbon monoxide is attributed mainly to an increase in concentration of carbon monoxide included in the gaseous fuel generated by the reformer or to an increase in gas utilization rate in the fuel cell. This structure reduces the concentration of carbon monoxide under the condition that the gas utilization rate exceeds the predetermined rate, thereby effectively canceling the catalyst poisoning and further improving the performance of the fuel cell.

In the fuel cell generator of essential structure, the carbon monoxide measurement means preferably comprises: an electrolyte membrane; first and second electrodes with a catalyst carried thereon, the first and second electrodes being arranged across the electrolyte membrane; a gaseous fuel supply conduit for supplying the gaseous fuel to the first electrode; an oxygen gas supply conduit for supplying an oxygen-containing gas to the second electrode; and potential difference detection means for measuring a potential difference between the first and second electrodes while a predetermined load is connected to the first and second electrodes.

The carbon monoxide measurement means of this structure measures the concentration of carbon monoxide by taking advantage of the principle of converting chemical energy to electrical energy in the fuel cell. A supply of gaseous fuel is fed to the first electrode via the gaseous fuel supply conduit, whereas an oxygen gas is fed to the second electrode via the oxygen gas supply conduit. The chemical energy of the gaseous fuel is converted to electrical energy by electrochemical reactions, and an electromotive force or potential difference is generated between the first and the second electrodes across the electrolyte membrane. In the carbon monoxide measurement means, a predetermined load is connected to the first and the second electrodes so as to make the electrochemical reactions continuously proceed. The potential difference detection means then measures the potential difference between the two electrodes. Like the known fuel cell, the potential difference detected by the potential difference detection means is decreased by poisoning of the catalyst with carbon monoxide. The potential difference accordingly represents the degree of catalyst poisoning and thereby the concentration of carbon monoxide.

The measurement of carbon monoxide by this principle is not affected by the presence of hydrogen. The carbon monoxide measurement means of this structure can accordingly measure, with high precision, the concentration of carbon monoxide included in a hydrogen-rich gas containing an extremely large amount of hydrogen and only a trace amount of carbon monoxide, such as a gaseous fuel fed to the fuel cell. This preferable structure appropriately controls the reformer to decrease the concentration of carbon monoxide without delay, thus effectively canceling the catalyst poisoning.

The invention is also directed to a method of generating electrical energy with a fuel cell comprising a pair of electrodes with a catalyst carried thereon. The method comprises the steps of:

(a) reforming an original fuel to generate a hydrogen-containing gaseous fuel;
(b) feeding the gaseous fuel to the electrodes of the fuel cell;
(c) measuring concentration of carbon monoxide included in the gaseous fuel; and
(d) controlling generation of the gaseous fuel in the step (a) according to the concentration of carbon monoxide measured in the step (c), thereby decreasing the concentration of carbon monoxide included in the gaseous fuel.

These and other objects, features, aspects, and advantages of the present invention will become more apparent from the following detailed description of the preferred embodiments with the accompanying drawings.

DESCRIPTION OF THE PREFERRED EMBODIMENT

Figure 1:
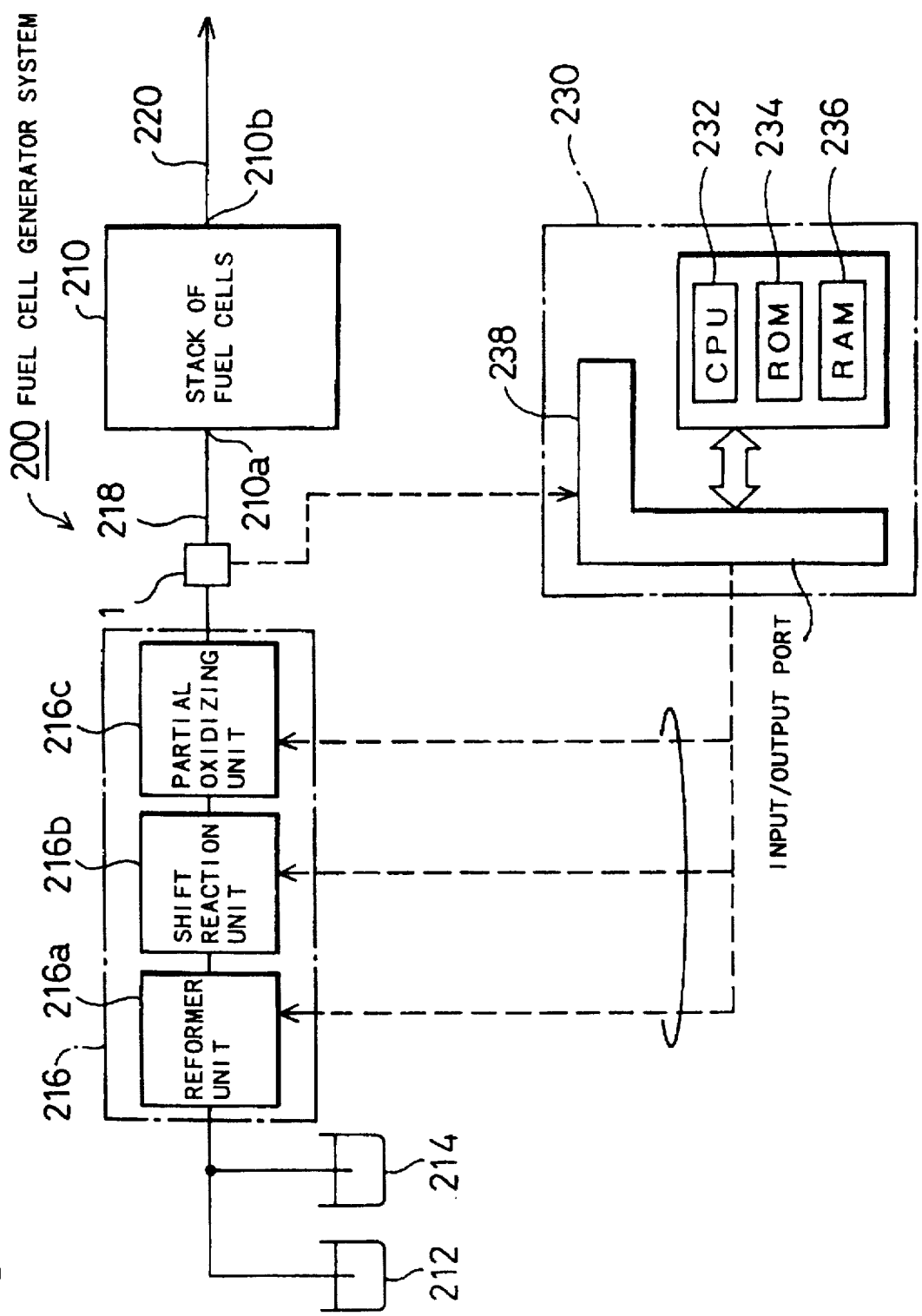
FIG. 1 is a block diagram illustrating structure of a fuel cell generator system 200 as a first embodiment according to the present invention.

FIG. 1 is a block diagram illustrating structure of a fuel cell generator system 200 as a first embodiment according to the present invention. The fuel cell generator system 200 includes a stack of polymer electrolyte fuel cells 210 for generating electrical energy, a reformer 216 for generating hydrogen-rich gas from methanol stored in a methanol reservoir 212 and water stored in a water reservoir 214, a gaseous fuel supply conduit 218 for feeding the hydrogen-rich gas generated by the reformer 216 as a gaseous fuel to the stack of fuel cells 210, and a gaseous fuel discharge conduit 220 for discharging the residual gas from the stack of fuel cells 210. The fuel cell generator system 200 is further provided with a carbon monoxide sensor 1 in the middle of the gaseous fuel supply conduit 218. An electronic control unit 230 receives output signals of the carbon monoxide sensor 1 and executes a variety of control processes.

A detailed structure of the carbon monoxide sensor 1 is given below.

Figure 2:
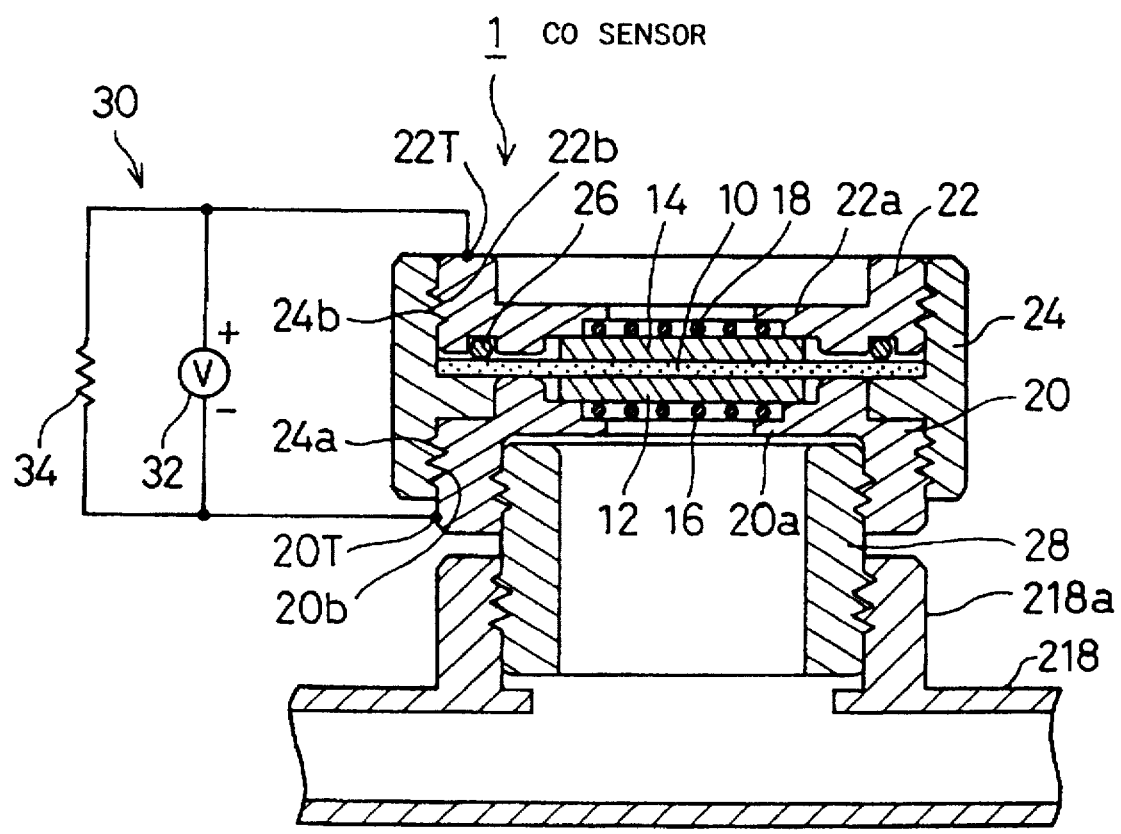
FIG. 2 is a vertical cross sectional view schematically illustrating structure of the carbon monoxide sensor 1 of the first embodiment.

FIG. 2 is a vertical cross sectional view illustrating a carbon monoxide sensor 1 as a first embodiment according to the invention. The carbon monoxide sensor 1 includes an electrolyte membrane 10, a pair of electrodes 12 and 14 arranged across the electrolyte membrane 10 to form a sandwich structure, a pair of meshed metal plates 16 and 18 disposed across the sandwich structure to prevent deflection of the sandwich structure, a pair of holders 20 and 22 for supporting the sandwich structure as well as the pair of meshed metal plates 16 and 18, and an insulating member 24 for connecting the holders 20 and 22 with each other under electrically insulating conditions.

The electrolyte membrane 10 is composed of solid polymer material, such as fluororesin, to be proton-conductive. The electrodes 12 and 14 are made of carbon cloth woven of carbon fibers, where carbon powder with platinum catalyst carried thereon is inserted into pores of the carbon cloth.

The electrolyte membrane 10 and the pair of electrodes 12 and 14 are joined together according to one of the following methods:

(1) Catalyst powder prepared in advance by making platinum carried on the surface of carbon powder is applied onto the surface of electrode bases (carbon cloth or carbon paper). The electrolyte membrane 10 and the electrode bases are then integrated by hot pressing.

(2) Catalyst powder prepared in advance by making platinum carried on the surface of carbon powder is applied onto the surface of electrode bases. The electrolyte membrane 10 and the electrode bases are subsequently joined together by means of a solution of proton-conductive solid polymer.

(3) Catalyst powder prepared in advance by making platinum carried on the surface of carbon powder is dispersed in an appropriate organic solvent to form paste. The paste is applied on the surface of the electrolyte membrane 10 by a known technique, like screen printing. The electrolyte membrane 10 and electrode bases are subsequently integrated by hot pressing.

(4) Platinum is carried on the surface of the electrolyte membrane 10 by sputtering, vapor deposition, CVD, PVD, or another method of thin film formation. The electrolyte membrane 10 and electrode bases are subsequently integrated by hot pressing.

Carbon powder with platinum catalyst carried thereon is prepared in the following manner. An aqueous solution of chloroplatinic acid is mixed with sodium thiosulfate to yield an aqueous solution of platinum sulfite complex. Hydrogen peroxide is added dropwise to the aqueous solution of platinum sulfite with stirring, so that platinum colloidal particles are deposited in the aqueous solution. Carbon black working as a carrier is then added to the aqueous solution with stirring, so that the platinum colloidal particles adhere to the surface of carbon black. Examples of applicable carbon black include Vulcan XC-72 (trade name by CABOT Corp., the U.S.A.) and Denka Black (trade name by DENKI KAGAKU KOGYO K.K). The carbon black with platinum particles adhering thereto is separated by filtration under reduced pressure or pressure filtration of the aqueous solution, washed repeatedly with deionized water, and completely dried at room temperature. The dried carbon black aggregate is ground with a grinder and heated in a reducing hydrogen atmosphere at 250° C. through 350° C. for approximately 2 hours for reduction of platinum on the carbon black and complete removal of the remaining chlorine.

The carrying density of platinum onto carbon black in the resulting platinum catalyst powder thus prepared, that is, the ratio of the weight of platinum carried on the carbon surface to the weight of carbon, is adjusted by varying the ratio of the quantity of chloroplatinic acid to the quantity of carbon black. Preparation of platinum catalyst powder is not limited to this method, but any other method is applicable as long as it ensures sufficient catalytic activities.

For the clarity of explanation, catalyst powder prepared above contains only platinum as a catalytic component. An alloy catalyst containing platinum as a primary component and one or the plural selected out of the group including ruthenium, nickel, cobalt, vanadium, palladium, indium, iron, chromium, and manganese, as a secondary component may, however, be used in place of platinum catalyst.

Preparation of platinum-ruthenium catalyst powder, that is, carbon black with platinum-ruthenium alloy catalyst carried thereon, is explained as an example of alloy catalyst. The platinum catalyst powder (carbon black with platinum catalyst carried thereon) prepared in the above manner is dispersed in deionized water with stirring. An aqueous solution of ruthenium chloride in limited amounts is added to the dispersion with stirring, and an aqueous solution of sodium carbonate in limited amounts is further added to the dispersion with stirring, so that ruthenium particles are deposited on the platinum catalyst-carrying carbon black. The platinum catalyst-carrying carbon black with ruthenium particles adhering thereto is separated by filtration under reduced pressure or pressure filtration of the solution mixture, washed repeatedly with deionized water, and sufficiently dried at room temperature. The dried carbon black aggregate is ground with a grinder and heated in a reducing hydrogen atmosphere at 250° C. through 350° C. for approximately 2 hours for reduction of platinum and ruthenium on the carbon black and complete removal of the remaining chlorine taken up during the deposition of ruthenium. The carbon black with platinum and ruthenium carried thereon is heated in a stream of inert gas (nitrogen or argon) at 800° C. through 900° C. for approximately 1 hour. This heating process makes an alloy of platinum and ruthenium on the carbon black and completes the platinum-ruthenium catalyst powder, that is, carbon black with platinum-ruthenium alloy catalyst carried thereon.

The amounts of platinum and ruthenium carried on carbon black are adjusted by varying the quantity of platinum-carrying carbon black and the quantity of ruthenium chloride. Preparation of platinum-rutheniumcatalyst powder is not limited to this method, but any other method is applicable as long as it ensures sufficient catalytic activities.

The preferable area of electrodes 12 and 14 ranges from 0.1 through 1.0 cm$^2$.

The meshed metal plates 16 and 18 have structure of allowing a gas to be flown into the electrodes 12 and 14. Preferable material for the meshed metal plates 16 and 18 has excellent electrical conductivity and good rust preventing properties and does not cause hydrogen brittleness; for example, titanium and stainless steel. Alternatively, the metal plates 16 and 18 may be meshed copper plates having surface coated with (for example, plated with) a metal like gold, platinum, or titanium. As long as the required properties including excellent electrical conductivity are satisfied, porous carbon plates, foamed nickel plates, and engineering plastics having surface coated with (for example, plated with) a metal like gold, platinum, or titanium may also be applicable as the metal plates 16 and 18.

The holders 20 and 22 respectively have flanges 20a and 22a projected inward from the cylindrical holder structures 20 and 22. The electrolyte membrane 10 and the pair of electrodes 12 and 14 as well as the meshed metal plates 16 and 18 are supported by these flanges 20a and 22a of the holders 20 and 22. Preferable material for the holders 20 and 22 has excellent electrical conductivity and good rust preventing properties and does not cause hydrogen brittleness; for example, titanium and stainless steel. As long as the required properties including excellent electrical conductivity are satisfied, copper plates and dense carbon plates or engineering plastics having surface coated with (for example, plated with) a metal like gold, platinum, or titanium may also be applicable as the holders 20 and 22.

The holder 22 is provided with an O-ring 26, which comes into contact with the electrolyte membrane 10 and prevents an atmosphere of one electrode from leaking to the other electrode. Another structure of ensuring the sealing properties may also be applicable instead of the O-ring 26; for example, an end portion of the electrolyte membrane 10 is applied to the holder 22 directly via an adhesive or by means of thermal contact bonding.

The holders 20 and 22 respectively have, on the circumference thereof, outer screw threads 20b and 22b, which mate and engage with internal screw threads 24a and 24b formed inside the insulating member 24. Engagement of the mating screw threads 20b,22b and 24a,24b connects the holders 20 and 22 with each other, where the holders 20 and 22 securely support the sandwich structure of electrode 12-electrolyte membrane 10-electrode 14 placed therebetween. Preferable material for the insulating member 24 is, for example, Teflon.

The carbon monoxide sensor 1 further includes a gas flow conduit 28 joined with one holder 20 through engagement of mating screw threads. The gas flow conduit 28 leads a gaseous fuel or object gas to be detected into the electrode 12 and is composed of insulating material. The other holder 22 does not connect with any specific gas conduit, but the electrode 14 is exposed to the atmosphere.

The carbon monoxide sensor 1 is also provided with a circuit 30, which electrically connects detection terminals 20T and 22T of the holders 20 and 22 with each other. The circuit 30 includes a voltmeter 32 and a resistor 34 for adjusting load current, which are arranged in parallel between the detection terminals 20T and 22T. Connection of the voltmeter 32 is determined to give negative polarity to the detection terminal 20T of the holder 20 on the side of the electrode 12 exposed to a gaseous fuel and positive polarity to the detection terminal 22T of the holder 22 on the side of the electrode 14 exposed to the atmosphere. Signals of the voltmeter 32 are output to an external control system.

The carbon monoxide sensor 1 thus constructed is linked through engagement of mating screw threads with a branched opening 40a of a gaseous fuel conduit 40 included in a fuel cell generator (not shown). The carbon monoxide sensor 1 is used for determining the concentration of carbon monoxide included in a supply of gaseous fuel fed to fuel cells (not shown).

The following description regards the process of detecting carbon monoxide included in a hydrogen-rich gaseous fuel (object gas to be detected) with the carbon monoxide sensor 1. A supply of gaseous hydrogen included in the hydrogen-rich gaseous fuel is fed to the electrode 12 of the carbon monoxide sensor 1, while a supply of oxygen included in the atmosphere is fed to the electrode 14. Reactions expressed by Equations (4) and (5) below accordingly proceed on the surface of the electrodes 12 and 14 across the electrolyte membrane 10:

$$H_2 \rightarrow 2H^+ + 2e^- \qquad (4)$$

$$2H^+ + 2e^- + (\tfrac{1}{2})O_2 \rightarrow H_2O \qquad (5)$$

These reactions are identical with those in fuel cells, which uses hydrogen and oxygen as fuels to generate electrical energy. An electromotive force is thus generated between the electrodes 12 and 14. Since the resistor 34 is connected to the electrodes 12 and 14 in this embodiment, the voltmeter 32 measures the potential difference between the electrodes 12 and 14 generated when a predetermined load is placed between the electrodes 12 and 14 and certain electric current is flown through the circuit. The potential difference decreases with an increase in concentration of carbon monoxide included in the gaseous fuel. This phenomenon is ascribed to the following reasons.

The reaction expressed by Equation (4) given above proceeds on the electrode 12, in which carbon powder with platinum catalyst carried thereon is inserted. Carbon monoxide existing in the gaseous fuel is adsorbed by the catalyst and interferes with the catalytic action, that is, poisons the catalyst. The degree of poisoning is large for the high concentration of carbon monoxide included in the gaseous fuel and small for the low concentration of carbon monoxide. The potential difference between the detection terminals 20T and 22T is measured, while the reactions expressed by Equations (4) and (5) continuously proceed on the electrodes 12 and 14. Since the potential difference reflects the concentration of carbon monoxide included in the gaseous fuel, the measurement of potential difference determines the concentration of carbon monoxide included in the gaseous fuel. The resistor 34 connecting one detection terminal 20T with the other detection terminal 22T allows the reactions of Equations (4) and (5) to continuously proceed on the electrodes 12 and 14, while the potential difference is measured between the detection terminals 20T and 22T.

Figure 3:
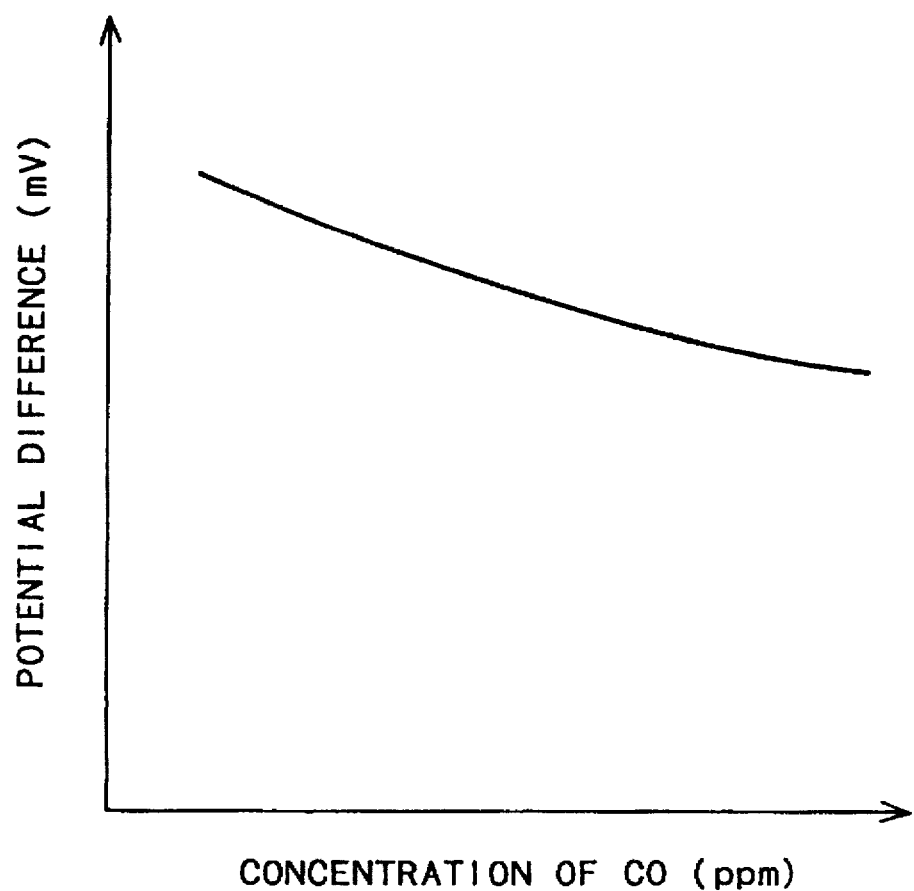
FIG. 3 is a graph showing a relationship between the concentration of carbon monoxide included in the gaseous fuel and the potential difference measured with the voltmeter 32.

A relationship between the concentration of carbon monoxide and the measurement of the voltmeter 32 is determined previously using gas containing known concentrations of carbon monoxide. The concentration of carbon monoxide included in the gaseous fuel is then determined according to this relationship. In accordance with a concrete structure, a map representing a relationship between the concentration of carbon monoxide included in the gaseous fuel and the potential difference measured by the voltmeter 32, for example, a map as shown in FIG. 3, is stored previously in a ROM of an electronic control unit. The electronic control unit refers to the map and executes logic operations to determine the concentration of carbon monoxide. The sensitivity of detection is not affected by the existence of hydrogen in this process of determining the concentration of carbon monoxide. The concentration of carbon monoxide included even in the hydrogen-rich reactant gas, such as a supply of gaseous fuel fed to fuel cells, can thus be determined with high precision.

Figure 4:
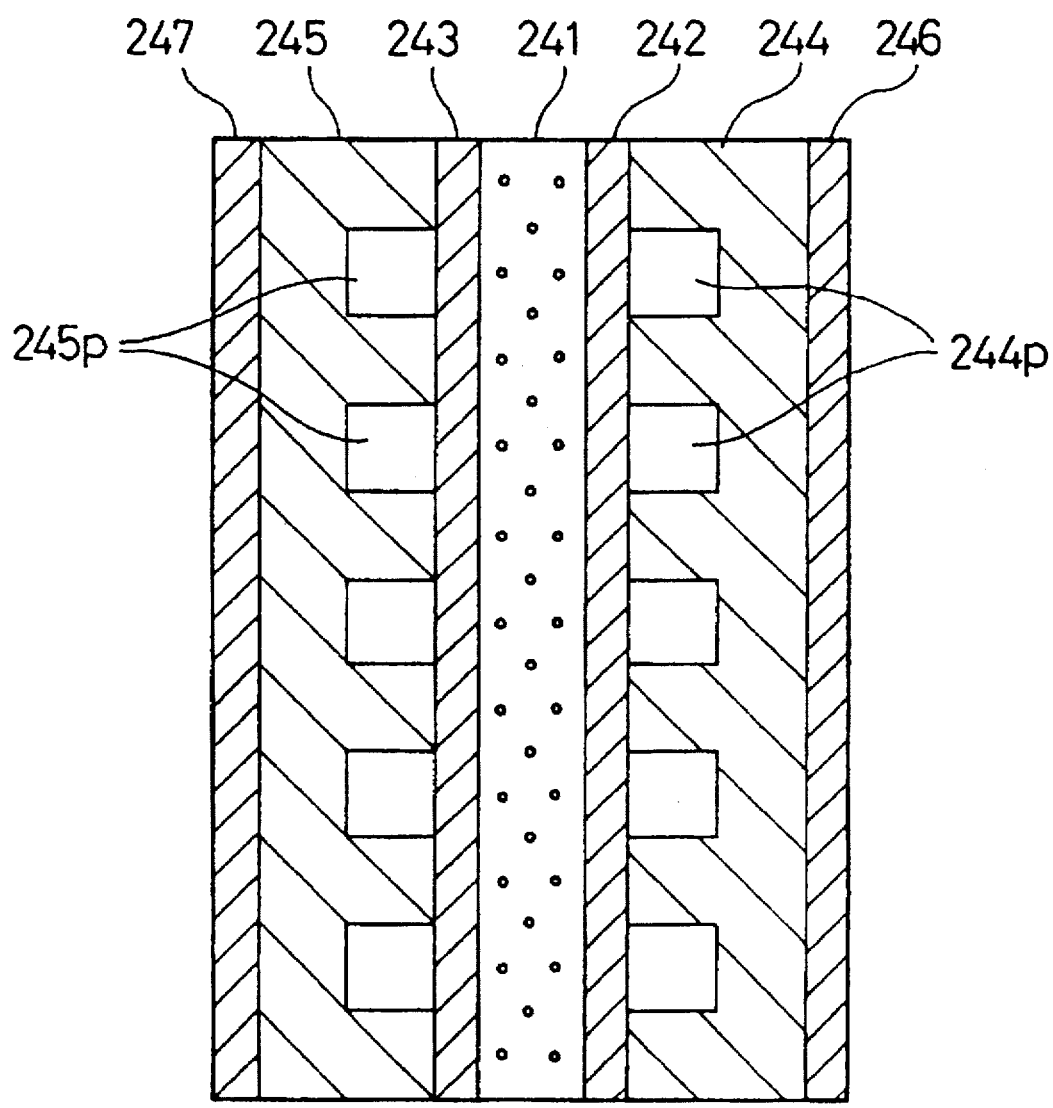
FIG. 4 is a cross sectional view illustrating a unit cell structure in the stack of fuel cells 210.

The stack of fuel cells 210 includes a plurality of polymer electrolyte fuel cells, whose unit cell structure is shown in FIG. 4. Each unit fuel cell includes an electrolyte membrane 241, an anode 242 and a cathode 243 arranged across the electrolyte membrane 241 to form a sandwich structure and work as gas diffusion electrodes, first and second separators 244 and 245 disposed across the sandwich structure and combined with the anode 242 and the cathode 243 to constitute flow paths of gaseous fuel and oxygen-containing gas, and first and second current collectors 246 and 247 disposed respectively outside the first and the second separators 244 and 245 to work as current-collecting electrodes of the anode 242 and the cathode 243.

The electrolyte membrane 241 is composed of solid polymer material, such as fluororesin, to be proton-conductive and shows a favorable electrical conductivity under the wet conditions. The anode 242 and the cathode 243 are made of carbon cloth woven of carbon fibers, where carbon powder with platinum catalyst or platinum-containing alloy catalyst carried thereon is inserted into the surface of the carbon cloth close to the electrolyte membrane 241 and into pores of the carbon cloth. The electrolyte membrane 241, the anode 242, and the cathode 243 are joined together to form a sandwich structure of anode 242-electrolyte membrane 241-cathode 243, in the same manner as the electrolyte membrane 10 and the two electrodes 12 and 14 in the carbon monoxide sensor 1 of the first embodiment.

The first separator 244 has a plurality of ribs, which constitute, in connection with the surface of the anode 242, a plurality of first channels 244p allowing flows of gaseous fuel. The second separator 245 also has a plurality of ribs, which constitute, in connection with the surface of the cathode 243, a plurality of second channels 245p allowing flows of oxygen-containing gas.

Each unit fuel cell in the stack of fuel cells 210 has the structure described above. In the actual configuration of the stack of fuel cells 210, plural sets of first separator 244/ anode 242/ electrolyte membrane 241/ cathode 243/ second separator 245 are laid one upon another, and the first and the second current collectors 246 and 247 are disposed outside the plural sets.

The gaseous fuel supply conduit 218 connects the reformer 216 with an anode-side gas inlet 210a of the stack of fuel cells 210. According to a concrete structure, the anode-side gas inlet 210a is connected to a manifold (not shown) and further to the plurality of first channels 244p for the flows of gaseous fuel in the stack of fuel cells 210 via the manifold. An anode-side gas outlet 210b of the stack of fuel cells 210 is also connected to another manifold (not shown) and further to the plurality of first channels 244p in the stack of fuel cells 210 via the manifold. The direction of connection of the gas outlet 210b is opposite to the direction of connection of the gaseous fuel supply conduit 218.

The reformer 216 includes: a reformer unit 216a allowing the reaction (expressed by Equation (1) above) of decomposing methanol to carbon monoxide and hydrogen and the reaction (expressed by Equation (2) above) of generating carbon dioxide and hydrogen from water and carbon monoxide generated by the decomposition reaction; a shift reaction unit 216b for making the residual, non-reacted carbon monoxide in the reformer unit 216a further react with water; and a partial oxidizing unit (also called as selective oxidizing unit) 216c for oxidizing the residual, non-reacted carbon monoxide in the shift reaction unit 216b. The units 216a through 216c of the reformer 216 are respectively connected to the electronic control unit 230.

The electronic control unit 230 is constructed as a logic circuit with a microcomputer. According to a concrete structure, the electronic control unit 230 includes: a CPU 232 for executing a variety of operations according to preset control programs; a ROM 234, in which control programs and control data required for the execution of various operations by the CPU 232 are previously stored; a RAM 236, which various data required for the execution of various operations by the CPU 232 are temporarily written in and read from; and an input/output port 238 for receiving output signals from the carbon monoxide sensor 1 and outputting control signals to the reformer unit 216a, the shift reaction unit 216b, and the partial oxidizing unit 216c of the reformer 216.

In the drawing of FIG. 1, only the gas system on the anode's side is shown and that on the cathode's side is omitted.

The CPU 232 of the electronic control unit 230 thus constructed receives output signals from the carbon monoxide sensor 1 and controls the reformer unit 216a, the shift reaction unit 216b, and the partial oxidizing unit 216c of the reformer 216 according to the output signals, so as to reform the quality of hydrogen-rich gas used as gaseous fuel.

Figure 5:
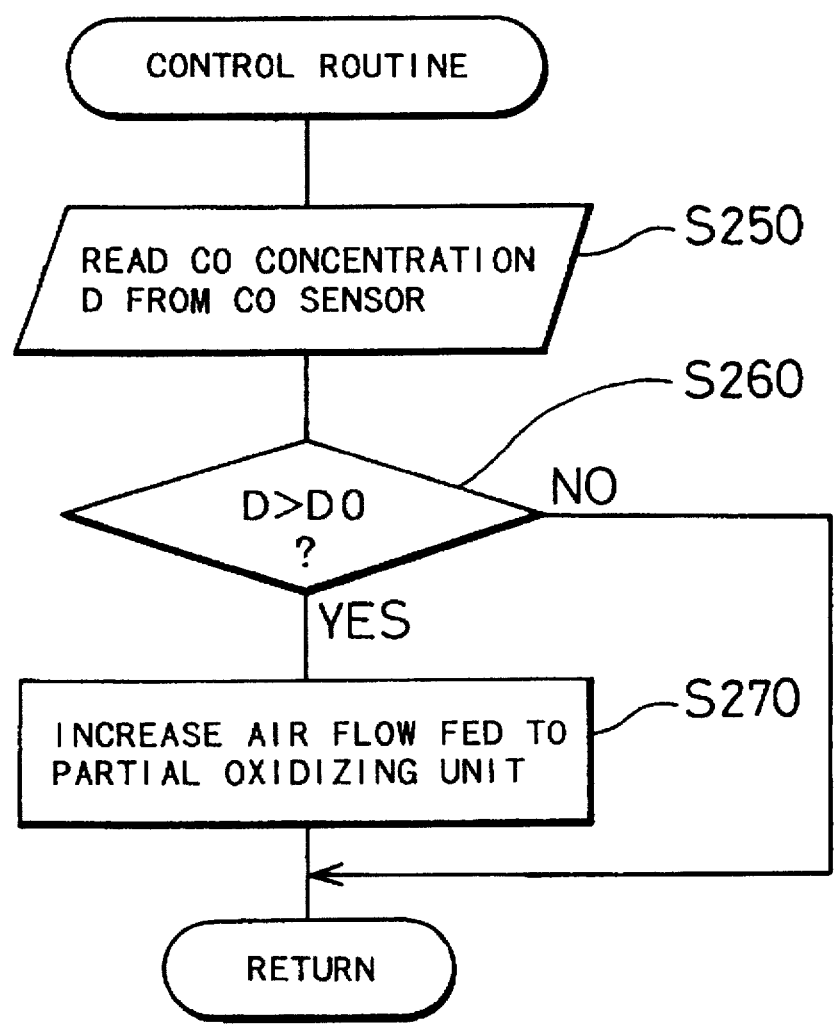
FIG. 5 is a flowchart showing a control routine executed by the CPU 232 of the electronic control unit 230 in the first embodiment.

FIG. 5 is a flowchart showing a control routine of reforming the hydrogen-rich gas. The control routine is repeatedly executed at predetermined time intervals. When the program enters the routine, the CPU 232 stores an output voltage from the voltmeter 32 of the carbon monoxide sensor 1 as a measured concentration D of carbon monoxide into the RAM 236 at step S250. The measured concentration D of carbon monoxide is then compared with a predetermined level D0 at step S260. In this embodiment, the predetermined level D0 is set equal to 20 [ppm] under an operating condition that the gas consumption ratio on the anode's side is 80[%].

When the measured concentration D of carbon monoxide is greater than the predetermined level D0 at step S260, the CPU 232 determines that the concentration of carbon monoxide from the reformer 216 is too high and executes a required process to lower the concentration of carbon monoxide discharged from the reformer 216.

Affirmative answer at step S260 leads the program to step S270, at which the CPU 232 transmits a control signal to the partial oxidizing unit 216c of the reformer 216 to increase a flow of air fed into the partial oxidizing unit 216c. The partial oxidizing unit 216c is driven at temperatures of 100° C. through 200° C. An increase in air flow fed into the reformed gas accelerates the reaction of oxidizing carbon monoxide included in the reformed gas to carbon dioxide. This results in lowering the concentration of carbon monoxide included in the reformed gas discharged from the partial oxidizing unit 216c. The program then goes to RETURN and exits from the control routine.

When the measured concentration D of carbon monoxide is not greater than the predetermined level D0 at step S260, on the other hand, the CPU 232 determines that the concentration of carbon monoxide from the reformer 216 is at an appropriate level. The program then goes to RETURN and exits from this control routine.

In the fuel cell generator system 200 of the third embodiment, the carbon monoxide sensor 1 determines the concentration of carbon monoxide included in the hydrogen-rich gas supplied to the stack of fuel cells 210. When the measured concentration D of carbon monoxide is greater than the predetermined level D0, the CPU 232 increases the flow of air fed into the partial oxidizing unit 216c of the reformer 216. This effectively lowers the concentration of carbon monoxide included in the hydrogen-rich gas fed to the stack of fuel cells 210, thereby relieving the catalyst poisoning in the stack of fuel cells 210.

An increase in the air flow fed into the reformed gas in the partial oxidizing unit 216c accelerates the oxidation reaction shown below:

$$2CO + O_2 \rightarrow 2CO_2 \qquad (6)$$

$$2H_2 + O_2 \rightarrow 2H_2O \qquad (7)$$

Such oxidation reaction relatively lowers the partial pressure of hydrogen included in the reformed gas. A relative decrease in partial pressure slightly lowers the output voltage from the stack of fuel cells 210. In a preferable structure, when the measured concentration D of carbon monoxide is restored to be smaller than the predetermined level D0, the air flow into the partial oxidizing unit 216c is returned to a stationary level.

In the structure of the third embodiment, the concentration of carbon monoxide included in the reformed gas is lowered by controlling the air flow fed into the partial oxidizing unit 216c. Other methods may, however, be applied to lower the concentration of carbon monoxide included in the reformed gas; for example, increasing the reaction temperature in the partial oxidizing unit 216c, increasing the reaction temperature in the reformer unit 216a, or controlling the reaction temperature in the shift reaction unit 216b.

The predetermined level D0 used for the comparison at step S260 depends upon the specifications of polymer electrolyte fuel cells (temperature of operation, type of catalyst, and gas consumption ratio). The predetermined level D0 is set by examining effects of a gaseous fuel containing a known concentration of carbon monoxide and flown into the fuel cell generator system (for example, a tank gas containing a known concentration of carbon monoxide), on the stack of fuel cells 210.

Figure 6:
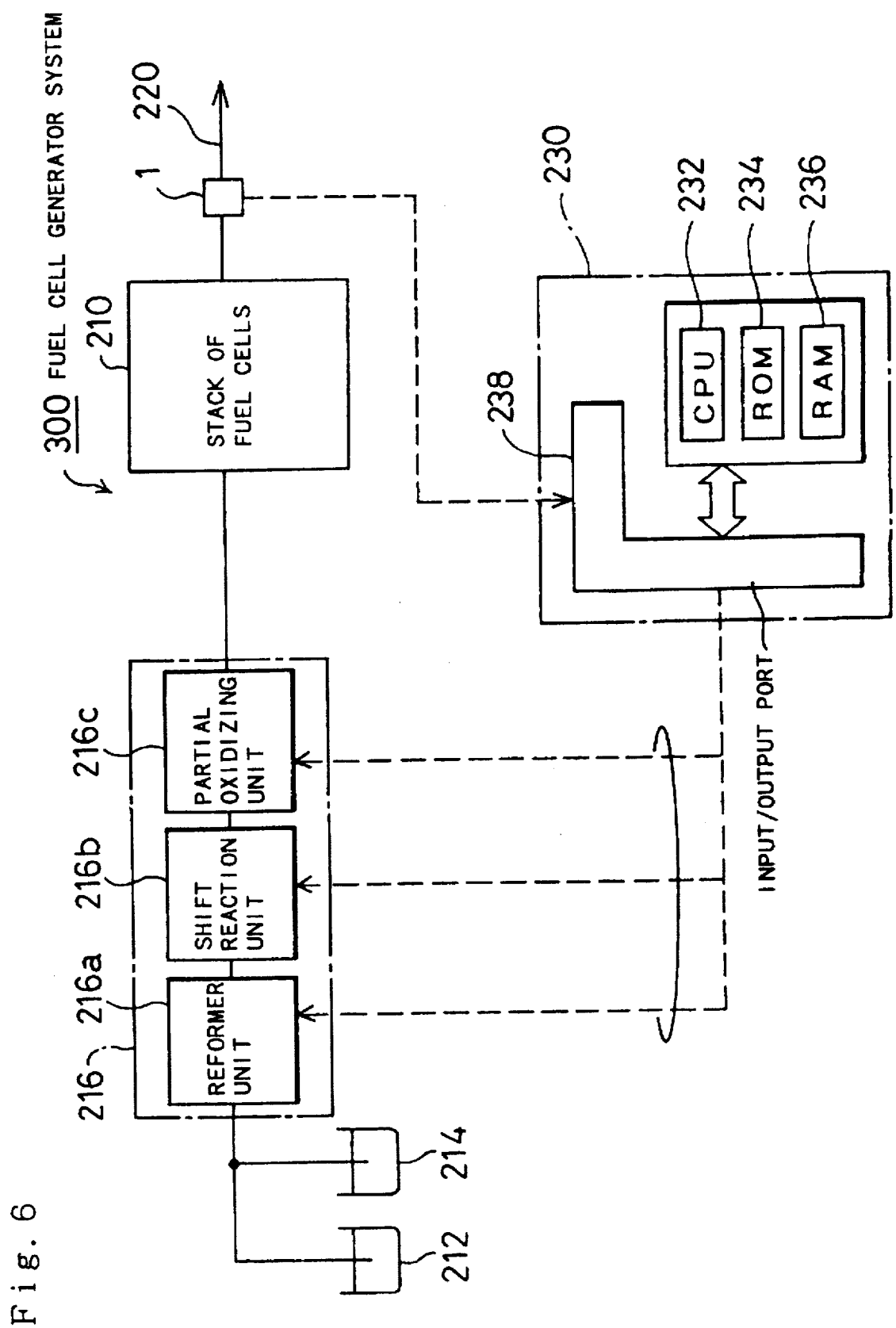
FIG. 6 is a block diagram illustrating structure of another fuel cell generator system 300 as a second embodiment according to the invention.

FIG. 6 is a block diagram illustrating structure of another fuel cell generator system 300 as a second embodiment according to the invention. The fuel cell generator system 300 of the second embodiment has a similar hardware structure to that of the first embodiment, except that the carbon monoxide sensor 1 is disposed at a different position. In the fuel cell generator system 300 of the second embodiment, the carbon monoxide sensor 1 is arranged in the middle of the gaseous fuel discharge conduit 220, instead of the gaseous fuel supply conduit 218.

While supplies of gaseous fuel generated in the reformer 216 and introduced into an anode-side gas inlet 210a of the stack of fuel cells 210 have identical gas flow and concentration of carbon monoxide, the difference in gas utilization rate in the stack of fuel cells 210 varies the concentration of carbon monoxide included in the gaseous fuel discharged from an anode-side gas outlet 210b of the stack of fuel cells 210. The gas utilization rate is defined as the rate amount of gaseous fuel required for the stack of fuel cells 210 to the flow of gaseous fuel fed to the stack. The gas utilization rate depends upon the load current density under the condition of identical gas flows.

Figure 7:
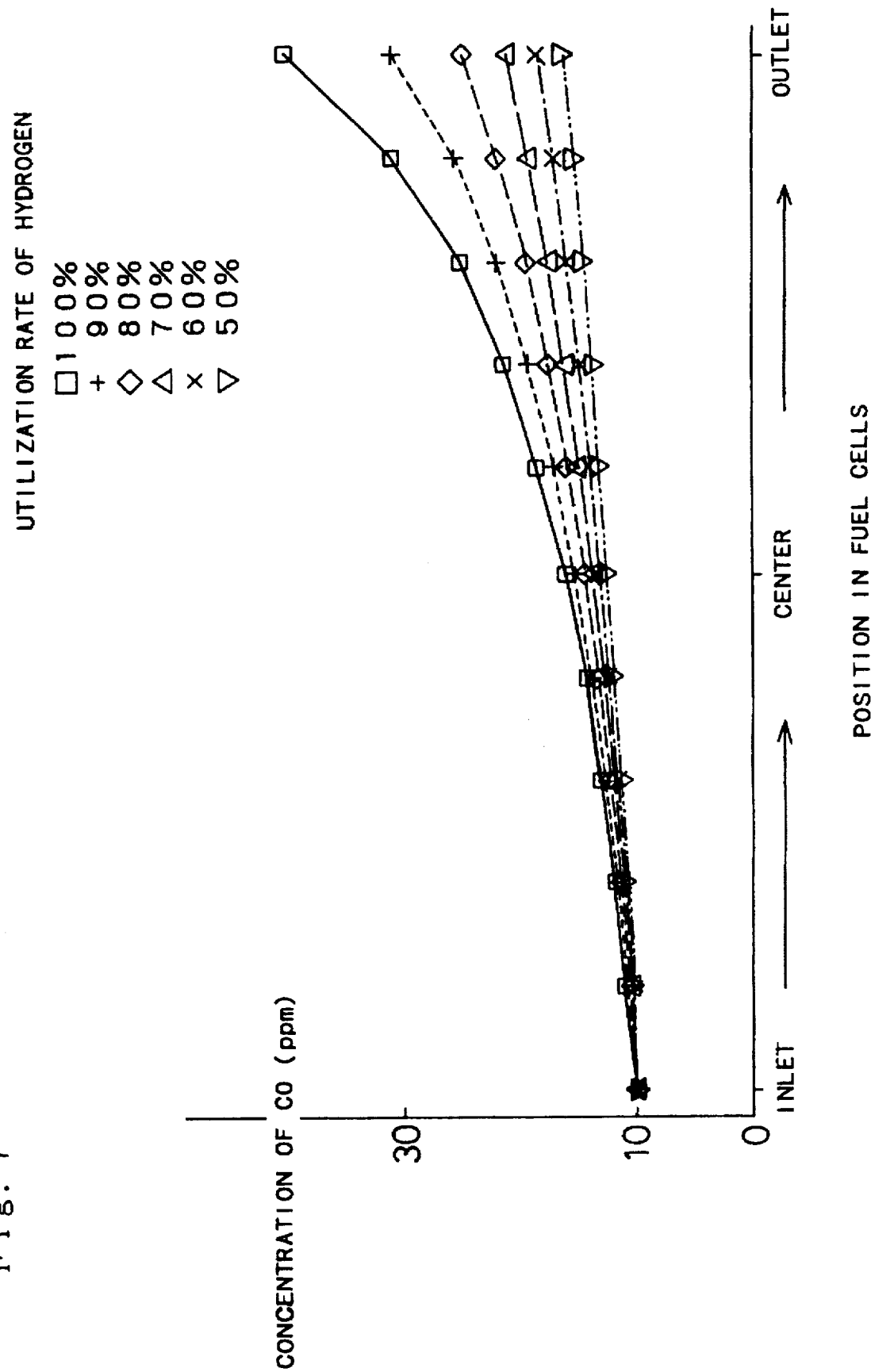
FIG. 7 is a graph showing the concentration of carbon monoxide plotted against the position in fuel cells at various utilization rates of hydrogen.

FIG. 7 is a graph showing the concentration of carbon monoxide plotted against the position in fuel cells at various utilization rates of hydrogen. The graph of FIG. 7 gives a calculated distribution of carbon monoxide concentration in polymer electrolyte fuel cells when a supply of methanol-reformed gas having a carbon monoxide concentration of 10 ppm and containing approximately 75% of hydrogen, approximately 25% of carbon dioxide is fed to the fuel cells. As clearly seen in the graph of FIG. 7, the concentration of carbon monoxide at the outlet is ten-odd ppm for the hydrogen utilization rate of 50% but reaches 40 ppm for the hydrogen utilization rate of 100%.

In this second embodiment, the carbon monoxide sensor 1 is disposed near to the anode-side gas outlet 210b of the stack of fuel cells 210, that is, in the middle of the gaseous fuel discharge conduit 220. Upon condition that the carbon monoxide sensors 1 have an identical detectable range of carbon monoxide, the structure of the second embodiment allows an increase in concentration of carbon monoxide to be detected at the earlier stage than the structure of the first embodiment, in which the carbon monoxide sensor 1 is disposed near to the anode-side gas inlet 210a, that is, in the middle of the gaseous fuel supply conduit 218. In the structure of the second embodiment, poisoning of catalyst is accordingly predictable at its earlier stage. A control routine executed in the second embodiment for reforming the quality of hydrogen-rich gaseous fuel as described in the first embodiment can thus more effectively cancel the poisoning of catalyst.

Figure 8:
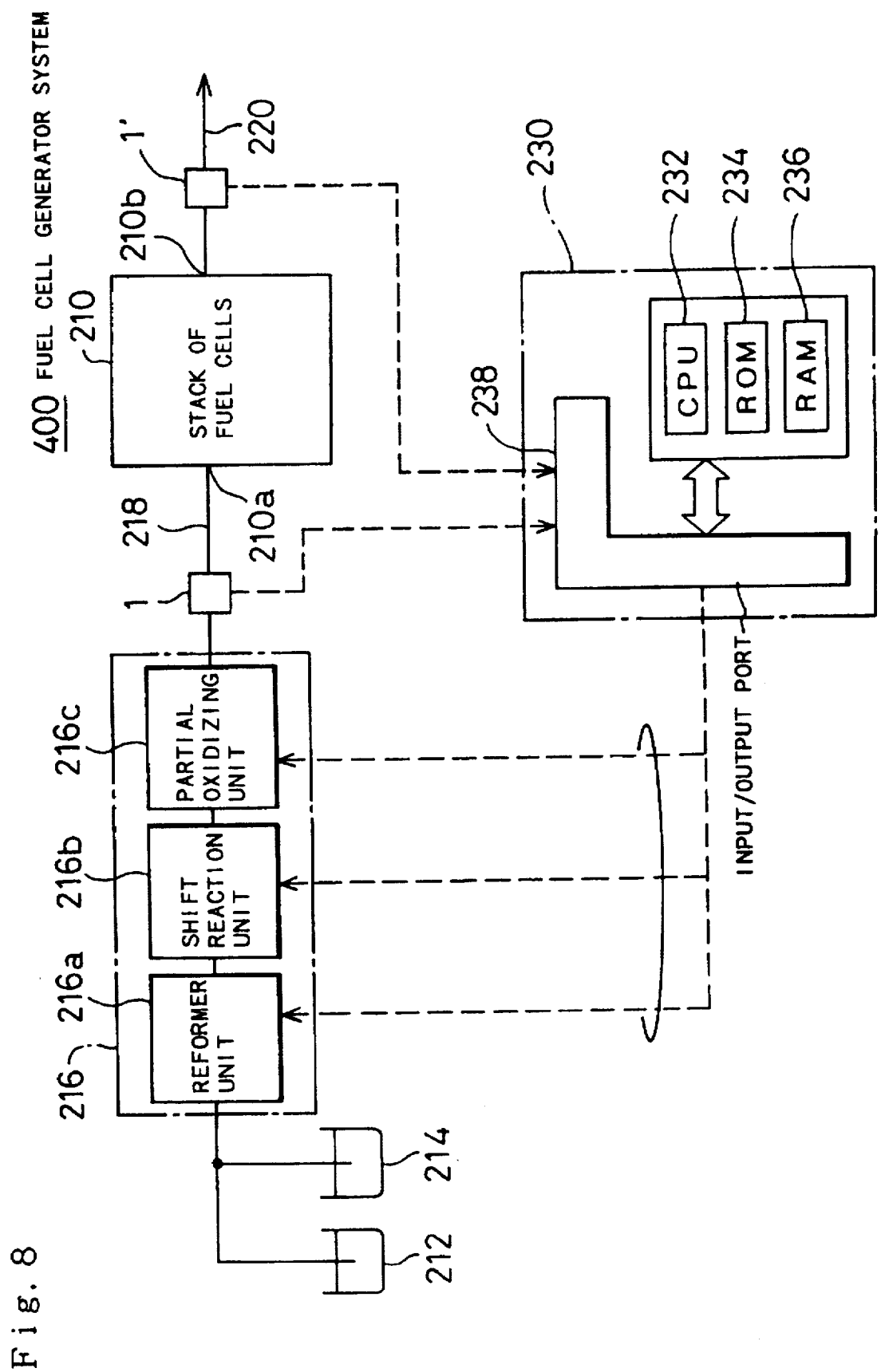
FIG. 8 is a block diagram illustrating structure of still another fuel cell generator system 400 as a third embodiment according to the invention.

FIG. 8 is a block diagram illustrating structure of still another fuel cell generator system 400 as a third embodiment according to the invention. The fuel cell generator system 400 of the third embodiment has a similar hardware structure to those of the first and the second embodiments, except that first and second carbon monoxide sensors 1 and 1' are arranged respectively in the middle of the gaseous fuel supply conduit 218 and in the middle of the gaseous fuel discharge conduit 220.

As described previously, the main advantage of arranging the carbon monoxide sensor 1' near to the anode-side gas outlet 210b of the stack of fuel cells 210 is to allow an increase in concentration of carbon monoxide to be detected at the earlier stage, compared with the arrangement of the carbon monoxide sensor 1 near to the anode-side gas inlet 210a, upon condition that the carbon monoxide sensors 1 and 1' have an identical detectable range of carbon monoxide. The earlier detection of an increase in carbon monoxide concentration is implemented, provided that the stack of fuel cells 210 is controlled to have a constant utilization rate of hydrogen. When the stack of fuel cells 210 is not controlled to have a constant utilization rate of hydrogen or when the control of the fuel cells stack 210 requires a relatively long response time, on the contrary, an increase in concentration of carbon monoxide at the anode-side gas outlet 210b of the stack of fuel cells 210 involves both an increase in concentration of carbon monoxide included in the gaseous fuel generated by the reformer 216 and an increase in hydrogen utilization rate in the stack of fuel cells 210.

In the structure of the third embodiment, the first and the second carbon monoxide sensors 1 and 1' are arranged respectively at the anode-side gas inlet 210a and the anode-side gas outlet 210b of the stack of fuel cells 210. This structure can effectively determine whether an increase in concentration of carbon monoxide is attributed to a variation in the quality of gaseous fuel generated by the reformer 216 or to an increase in hydrogen utilization rate in the stack of fuel cells 210, thereby ensuring appropriate system control.

Figure 9:
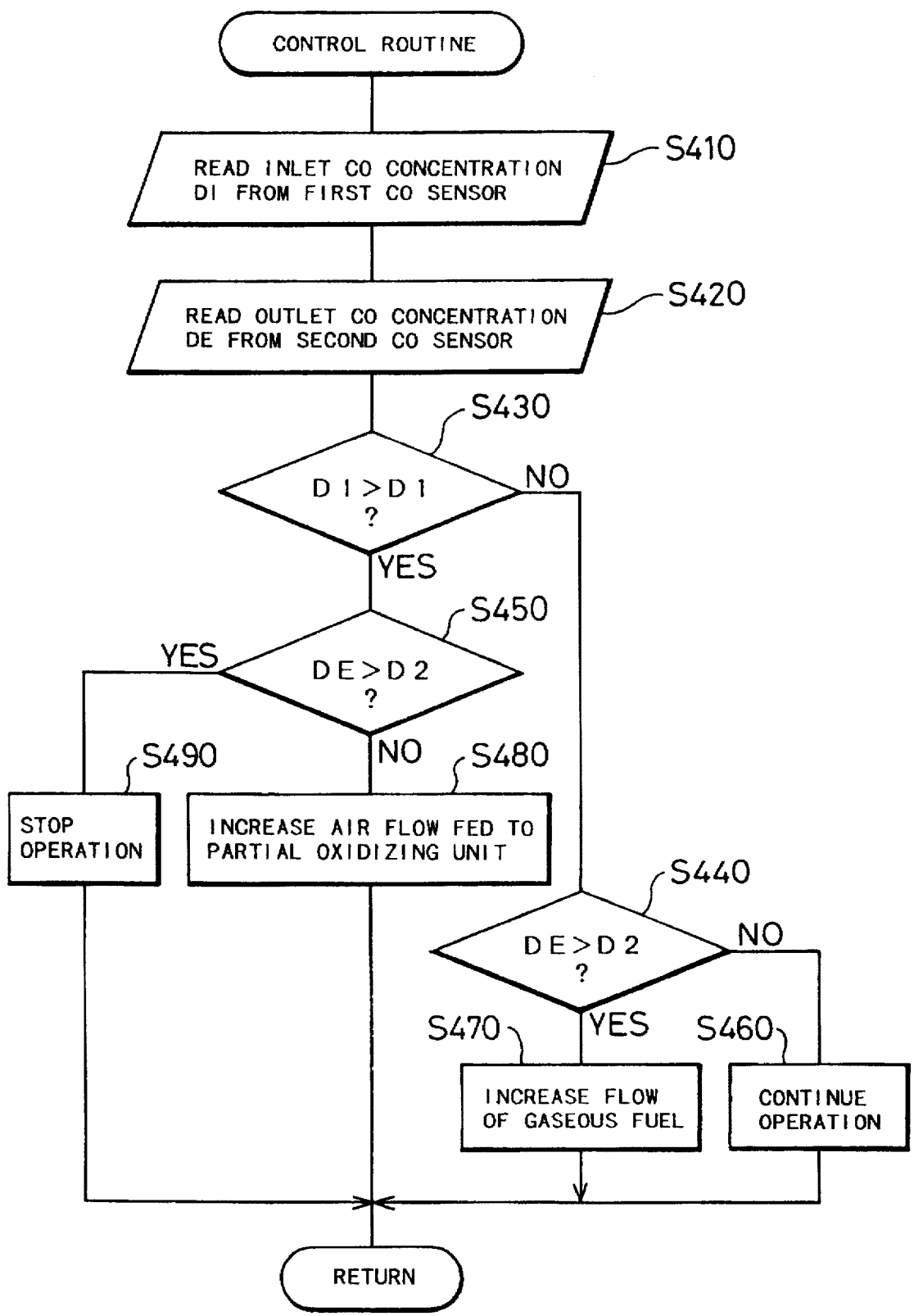
FIG. 9 is a flowchart showing a control routine executed by the CPU 232 of the electronic control unit 230 in the third embodiment.

The electronic control unit 230 in the third embodiment receives output signals from the first carbon monoxide sensor 1 arranged in the gaseous fuel supply conduit 218 and from the second carbon monoxide sensor 1' arranged in the gaseous fuel discharge conduit 220, and executes a required control process based on these output signals. FIG. 9 is a flowchart showing details of the control routine executed by the electronic control unit 230 in the third embodiment. The control routine of FIG. 9 is repeatedly executed at predetermined time intervals.

When the program enters the routine of FIG. 9, the CPU 232 receives an output voltage sent from the first carbon monoxide sensor 1 disposed in the gaseous fuel supply conduit 218, and stores the output voltage as an inlet carbon monoxide concentration DI into the RAM 236 at step S410. The CPU 232 then receives an output voltage sent from the second carbon monoxide sensor 1' disposed in the gaseous fuel discharge conduit 220, and stores the output voltage as an outlet carbon monoxide concentration DE into the RAM 236 at step S420.

The program proceeds to step S430 at which the inlet carbon monoxide concentration DI input at step S410 is compared with a predetermined first concentration D1 and subsequently to step S440 or step S450 at which the outlet carbon monoxide concentration DE input at step S420 is compared with a predetermined second concentration D2. Upon condition that the stack of fuel cells 210 is operated with the gas utilization rate of 80[%] on the anode's side, the predetermined first concentration D1 is equal to 20 [ppm] and the predetermined second concentration D2 is equal to 50 [ppm].

When the inlet carbon monoxide concentration DI is determined to be not greater than the predetermined first concentration D1 at step S430 and the outlet carbon monoxide concentration DE is determined to be not greater than the predetermined second concentration D2 at step S440, the program proceeds to step S460 to continue operation of the fuel cell generator system 400. In this case, the CPU 232 determines that the concentration of carbon monoxide in the anode's gas system does not significantly affect the operation of the fuel cell generator system 400 and allows the fuel cell generator system 400 to continue operation under the current operating conditions.

When the inlet carbon monoxide concentration DI is determined to be not greater than the predetermined first concentration D1 at step S430 but the outlet carbon monoxide concentration DE is determined to be greater than the predetermined second concentration D2 at step S440, on the other hand, the program proceeds to step S470. Under these conditions, it is determined that the gas utilization rate in the stack of fuel cells 210 is relatively high and that a decrease in amount of gaseous hydrogen released from the anode-side gas outlet 210b increases the outlet carbon monoxide concentration DE. At step S470, the CPU 232 accordingly increases the flow of gaseous fuel fed to the stack of fuel cells 210 so as to decrease the gas utilization rate, thereby lowering the concentration of carbon monoxide included in the gaseous discharge from the stack of fuel cells 210. Increasing the flow of gaseous fuel is implemented by controlling the reformer 216, the methanol reservoir 212, or the water reservoir 214 according to a known process, whose description is omitted here.

When the inlet carbon monoxide concentration DI is determined to be greater than the predetermined first concentration D1 at step S430 and the outlet carbon monoxide concentration DE is determined to be not greater than the predetermined second concentration D2 at step S450, the program proceeds to step S480. Under these conditions, it is determined that the gaseous fuel generated by the reformer 216 includes high concentration of carbon monoxide and that the gas utilization rate in the stack of fuel cells 210 is relatively low. At step S480, the CPU 232 accordingly controls the reformer 216 in order to decrease the concentration of carbon monoxide included in the gaseous fuel generated therefrom. According to a concrete procedure, the CPU 232 increases the air flow fed to the partial oxidizing unit 216c of the reformer 216, in the same manner as step S270 in the first embodiment. During this control procedure, the load current is preferably regulated so as to prevent the gas utilization rate in the stack of fuel cells 210 from undesirably increasing.

When the inlet carbon monoxide concentration DI is determined to be greater than the predetermined first concentration D1 at step S430 and the outlet carbon monoxide concentration DE is determined to be greater than the predetermined second concentration D2 at step S450, the program proceeds to step S490. Under these conditions, it is determined that the gaseous fuel generated by the reformer 216 includes high concentration of carbon monoxide and that the gas utilization rate in the stack of fuel cells 210 is relatively high. Based on the judgment that there is no hope of recovery from catalyst poisoning, the CPU 232 stops operation of the fuel cell generator system 400 in safety while releasing a load (not shown) from the fuel cells stack 210. The CPU 232 determines that the concentration of carbon monoxide included in the gaseous fuel has reached the level to interfere with continuous operation of the fuel cell generator system 400, and accordingly ceases operation of the fuel cell generator system 400.

According to a concrete procedure of suspending the fuel cell generator system 400, the load connected to the stack of fuel cells 210 is securely released while supplies of electricity are changed from the load to a secondary cell, such as a lead-acid accumulator (not shown), connected in parallel to the stack of fuel cells 210. The stack of fuel cells 210 and the peripheral equipment are then ceased safely. In response to the judgment of critical catalyst poisoning on the anode's side of the stack of fuel cells 210 due to a significant increase in concentration of carbon monoxide, the CPU 232 urgently stops operation of the stack of fuel cells 210 and protects the stack of fuel cells 210, the peripheral equipment, and the load connected to the fuel cells stack 210 from unexpected damages. One method of urgently stopping the stack of fuel cells 210 is to inject a purge of nitrogen or an inert gas, such as argon.

The fuel cell generator system 400 of the third embodiment thus constructed can determine whether an increase in concentration of carbon monoxide on the anode's side is attributed to a variation in the quality of gaseous fuel generated by the reformer 216 or to an increase in hydrogen utilization rate in the stack of fuel cells 210. This structure adequately lowers the concentration of carbon monoxide according to its primary cause, thus securely canceling the catalyst poisoning.

Figure 10:
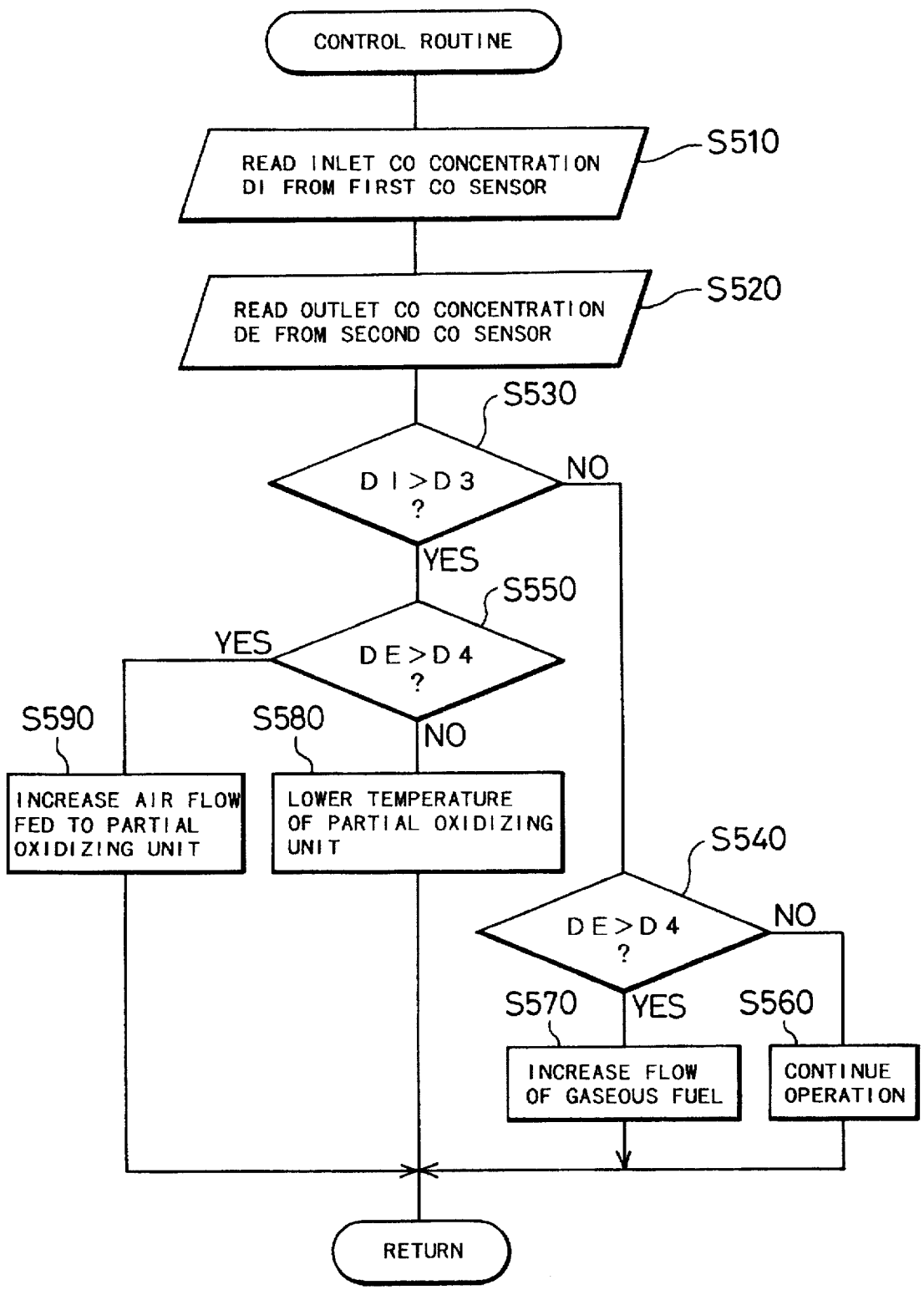
FIG. 10 is a flowchart showing a control routine executed by the CPU 232 of the electronic control unit 230 in a fourth embodiment of the invention.

A fuel cell generator system given as a fourth embodiment according to the invention has an identical hardware structure with that of the fuel cell generator system 400 of the third embodiment, while the CPU 232 of the electronic control unit 230 in the fourth embodiment executes a different control routine from that of the third embodiment. FIG. 10 is a flowchart showing details of the control routine executed by the electronic control unit 230 in the fourth embodiment, which is repeatedly executed at predetermined time intervals.

The processes at steps S510, S520, S560, and S570 in the control routine of FIG. 10 are identical with those at steps S410, S420, S460, and S470 in the control routine of FIG. 9 of the third embodiment. The processes at steps S530 through S550 in the flowchart of FIG. 10 are similar to those at steps S430 through S450 in the flowchart of FIG. 9, except that the predetermined first concentration D1 is replaced by a predetermined third concentration D3, and the predetermined second concentration D2 by a predetermined fourth concentration D4. The predetermined third concentration D3 is set to be smaller than the predetermined first concentration D1, whereas the predetermined fourth concentration D4 is smaller than the predetermined second concentration D2. Upon condition that the stack of fuel cells 210 is operated with the gas utilization rate of 80[%] on the anode's side, the predetermined third concentration D3 is equal to 10 [ppm] and the predetermined fourth concentration D4 is equal to 25 [ppm]. In the structure of the fourth embodiment, smaller values are set as the reference concentrations to be compared with the inlet and output carbon monoxide concentrations DI and DE. This allows an increase in concentration of carbon monoxide to be detected at its earlier stage and secures a longer period of time before an actual influence on the stack of fuel cells 210.

In the flowchart of the fourth embodiment, when the inlet carbon monoxide concentration DI is determined to be greater than the predetermined third concentration D3 at step S530 and the outlet carbon monoxide concentration DE is determined to be not greater than the predetermined fourth concentration D4 at step S550, the program proceeds to step S580, which is different from step S480 of the third embodiment.

It is determined that an increase in concentration of carbon monoxide included in the gaseous fuel generated by the reformer 216 does not immediately affect the operation of the stack of fuel cells 210. At step S580, the CPU 232 accordingly controls the reformer 216 to decrease the concentration of carbon monoxide to or below a predetermined level, while continuing the operation of the stack of fuel cells 210. Since there is sufficient time to reduce the concentration of carbon monoxide, any measure having an effect on the decrease in concentration of carbon monoxide with a slower response may be taken. For example, the CPU 232 lowers the temperature of the partial oxidizing unit 216c of the reformer 216.

When the inlet carbon monoxide concentration DI is determined to be greater than the predetermined third concentration D3 at step S530 and the outlet carbon monoxide concentration DE is determined to be greater than the predetermined fourth concentration D4 at step S550, on the other hand, the program proceeds to step S590, which is different from step S490 of the third embodiment.

It is determined that the concentration of carbon monoxide included in the gaseous fuel on the anode's side generated by the reformer 216 exceeds a predetermined level and that there is insufficient time to reduce the concentration of carbon monoxide. At step S590, the CPU 232 accordingly takes a measure of having an effect on the decrease in concentration of carbon monoxide with a quicker response, for example, increases the air flow fed to the partial oxidizing unit 216c of the reformer 216.

The fuel cell generator system of the fourth embodiment thus constructed can detect an increase in concentration of carbon monoxide on the anode's side at its earlier stage, thereby preventing catalyst poisoning without delay and effectively canceling the catalyst poisoning.

In the fourth embodiment, even when the concentration of carbon monoxide increases both at the inlet and outlet of the stack of fuel cells 210, the CPU 232 does not stop operation of the fuel cell generator system but tries to decrease the concentration of carbon monoxide. In a preferable structure, however, when these conditions continue for a predetermined time period, the CPU 232 determines that there is no hope of recovery from catalyst poisoning and stops operation of the fuel cell generator system in the same manner as step S490 in the control routine of the third embodiment.

Figure 11:
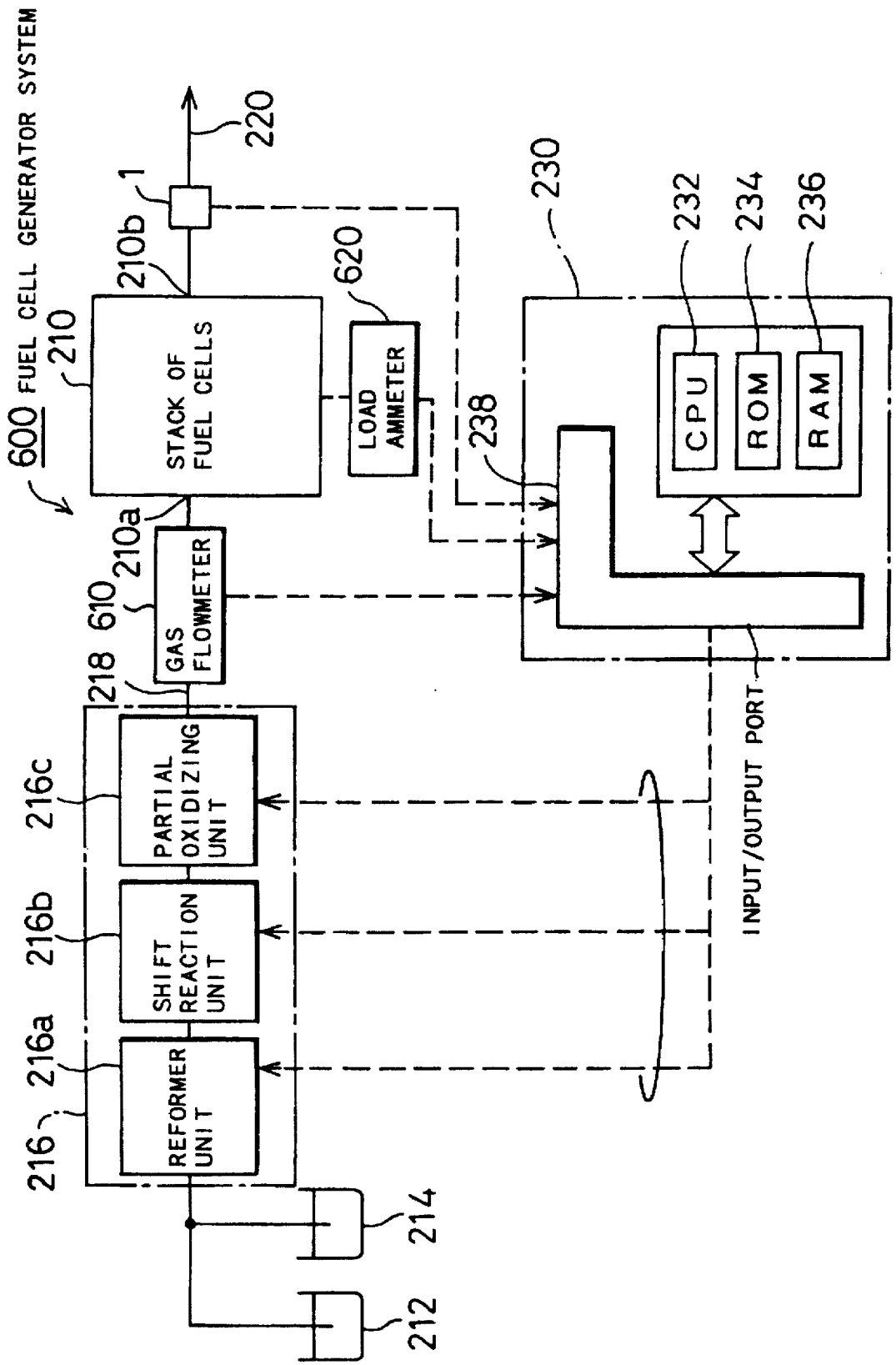
FIG. 11 is a block diagram illustrating structure of another fuel cell generator system 600 as a fifth embodiment according to the invention.

FIG. 11 is a block diagram illustrating structure of another fuel cell generator system 600 as a fifth embodiment according to the invention. Like the fuel cell generator system 300 of the second embodiment, in the fuel cell generator system 600 of the fifth embodiment, the carbon monoxide sensor 1 is arranged near to the anode-side gas outlet 210b of the stack of fuel cells 210, that is, in the middle of the gaseous fuel discharge conduit 220. The fuel cell generator system 600 is further provided with a gas flowmeter 610 disposed near to the anode-side gas inlet 210a for measuring the flow of gaseous fuel fed to the stack of fuel cells 210, and a load ammeter 620 connected to the stack of fuel cells 210 for measuring the output current of the fuel cells stack 210. The other hardware structure of the fifth embodiment is identical with that of the fuel cell generator system 300 of the second embodiment.

The electronic control unit 230 receives output signals from the carbon monoxide sensor 1, the gas flowmeter 610, and the load ammeter 620, and executes a required control process based on these output signals.

Figure 12:
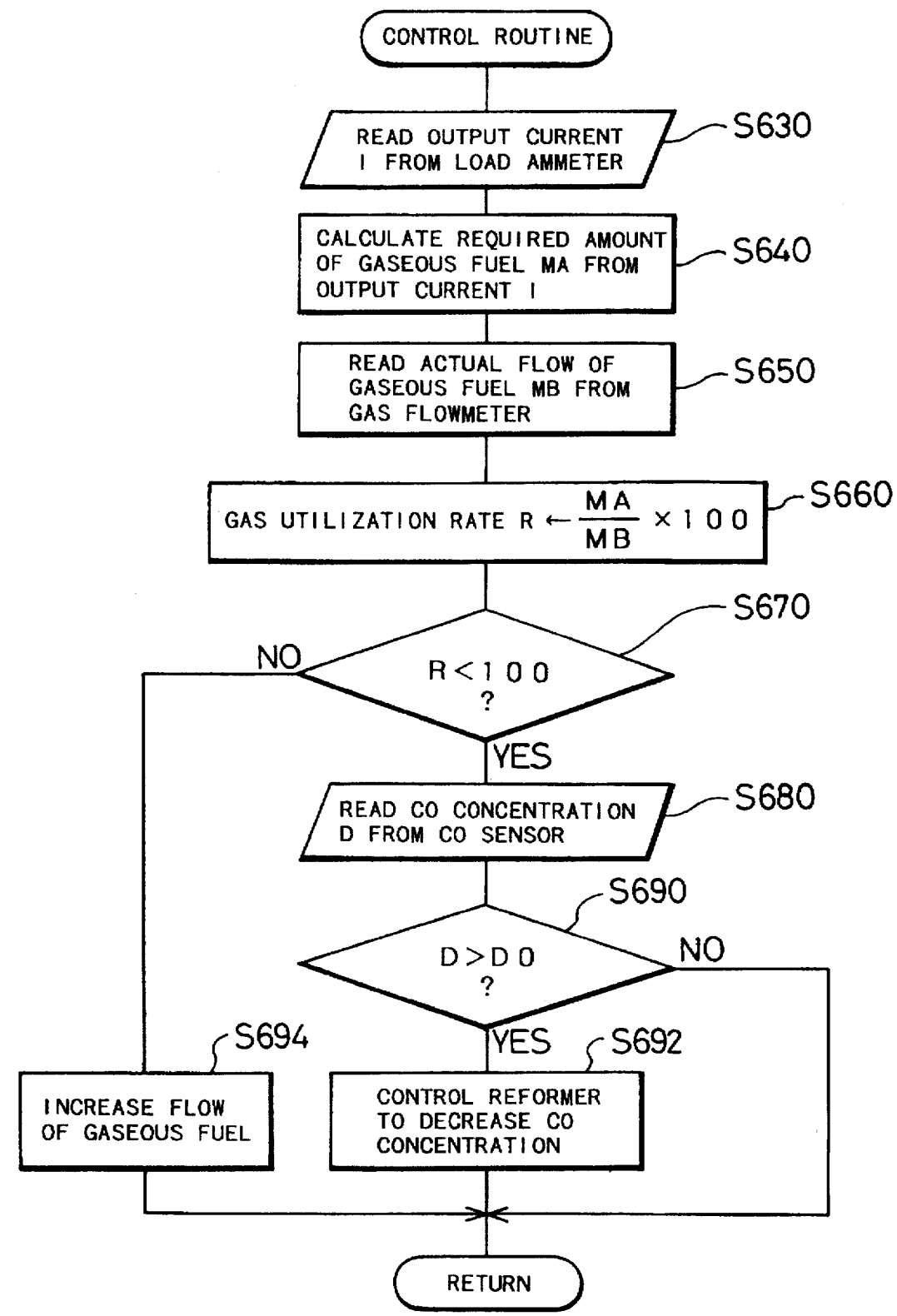
FIG. 12 is a flowchart showing a control routine executed by the CPU 232 of the electronic control unit 230 in the fifth embodiment.

FIG. 12 is a flowchart showing details of the control routine executed by the electronic control unit 230 in the fifth embodiment. The control routine of FIG. 12 is repeatedly executed at predetermined time intervals. When the program enters the routine, the CPU 232 of the electronic control unit 230 first reads the load ammeter 620 to input an output current I of the stack of fuel cells 210 at step S630, and calculates from the output current I a required amount of gaseous fuel MA, which is theoretically required for the stack of fuel cells 210, at step S640. The program then proceeds to step S650, at which the CPU 232 reads the gas flowmeter 610 to input a gas flow MB actually fed to the stack of fuel cells 210.

At subsequent step S660, the CPU 232 calculates a gas utilization rate R from the required amount of gaseous fuel MA calculated at step S640 and the gas flow MB obtained at step S650 according to Equation (8) given below:

$$R = MA/MB \times 100 [\%] \tag{8}$$

The CPU 232 then determines at step S670 whether the gas utilization rate R calculated is less than 100[%]. When the gas utilization rate R is less than 100[%] at step S670, the program goes to step S680 and executes the process of steps S680 to S692 to control the concentration of carbon monoxide.

The CPU 232 reads the carbon monoxide sensor 1 to input a concentration of carbon monoxide D at step S680, and compares the carbon monoxide concentration D obtained at step S680 with a predetermined level D0 at step S690. When the carbon monoxide concentration D is greater than the predetermined level D0 at step S690, the program goes to step S692, at which the CPU 232 determines that the gaseous fuel generated by the reformer 216 includes carbon monoxide of an excessive concentration, and controls the reformer 216 to decrease the concentration of carbon monoxide included in the gaseous fuel. Possible measures taken to decrease the concentration of carbon monoxide involve increasing the air flow fed to the partial oxidizing unit 216c of the reformer 216 or lowering the temperature of the partial oxidizing unit 216c.

After the execution of step S692, the program goes to RETURN and exits from the routine. When the carbon monoxide concentration D is not greater than the predetermined level D0 at step S690, on the contrary, the CPU 232 determines that the gaseous fuel generated by the reformer 216 includes carbon monoxide of an acceptable concentration and the program directly goes to RETURN.

When the gas utilization rate R is not less than 100[%] at step S670, the amount of gaseous hydrogen released from the anode-side gas outlet 210b is significantly decreased, so that the carbon monoxide concentration D can not appropriately reflect the concentration of carbon monoxide included in the gaseous fuel fed to the stack of fuel cells 210. The gas utilization rate R of not less than 100[%] leads the program to step S694, at which the CPU 232 increases the flow of gaseous fuel fed to the stack of fuel cells 210, thereby decreasing the gas utilization rate below 100[%]. After the execution of step S694, the program goes to RETURN and exits from the routine.

In the control routine of the fifth embodiment, output signals of the carbon monoxide sensor 1 disposed after the stack of fuel cells 210 are used only when the gas utilization rate is less than 100[%] in the stack of fuel cells 210. This structure allows the CPU 232 to determine that a decrease in concentration of carbon monoxide is attributed not to a decrease in gas utilization rate R but to the catalyst poisoning by carbon monoxide included in the gaseous fuel generated by the reformer 216.

When the measurement of the carbon monoxide sensor 1 shows high concentration of carbon monoxide included in the gaseous fuel at the anode-side gas outlet 210b of the stack of fuel cells 210, the fuel cell generator system 600 of the fifth embodiment controls the reformer 216 to securely cancel the catalyst poisoning.

Figure 13:
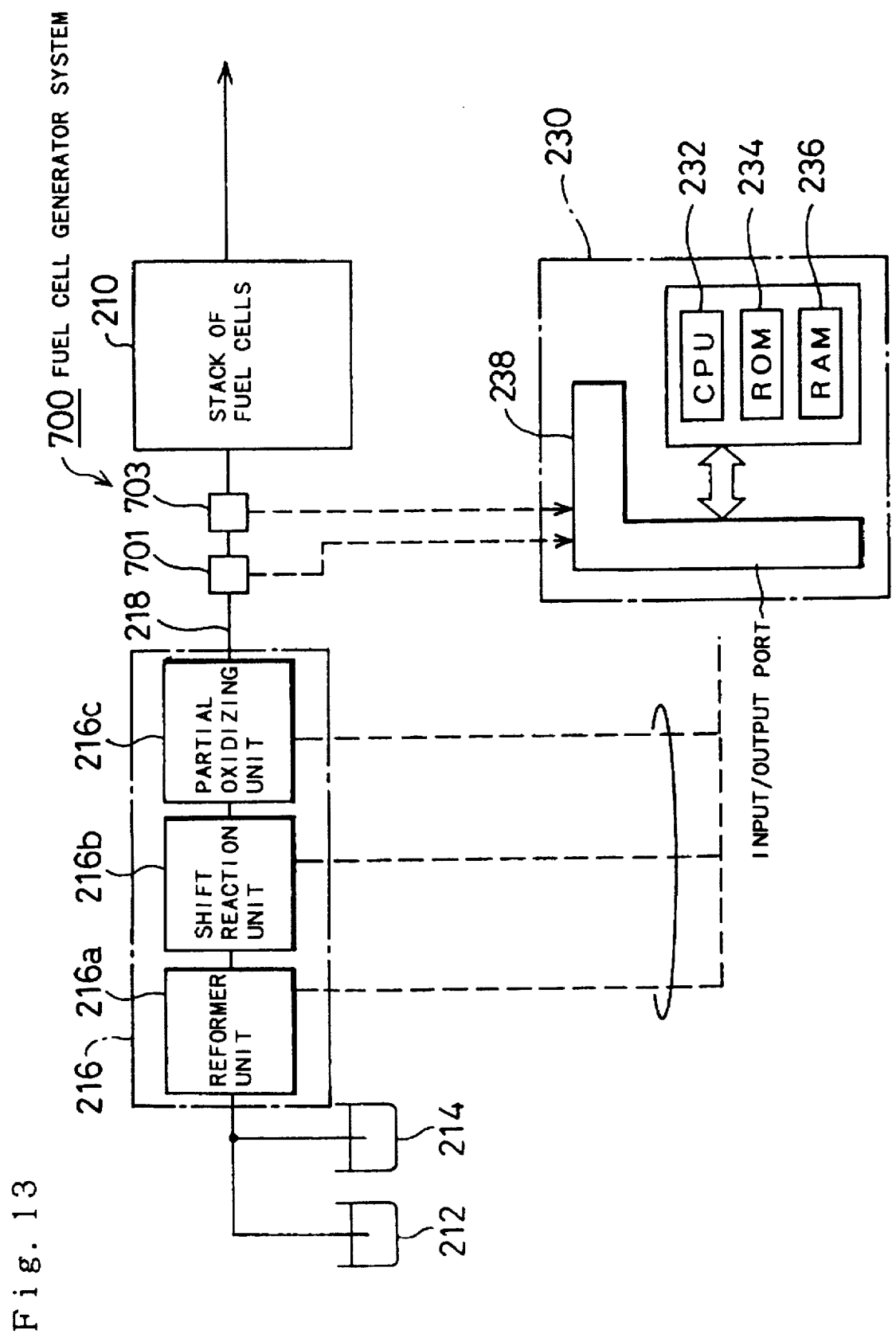
FIG. 13 is a block diagram illustrating structure of another fuel cell generator system 700 as a sixth embodiment according to the invention.

FIG. 13 is a block diagram illustrating structure of another fuel cell generator system 700 as a sixth embodiment according to the invention. The fuel cell generator system 700 of the sixth embodiment has a similar hardware structure to that of the fuel cell generator system 200 of the first embodiment, except that two carbon monoxide sensors 701 and 703 with different sensitivities of detection are arranged in the gaseous fuel supply conduit 218.

Different sensitivities imply different detectable concentrations of carbon monoxide. Sensors of the low detectable concentration represent those with high sensitivity of detection, whereas sensors of the high detectable concentration represent those with low sensitivity of detection. In the sixth embodiment, the first carbon monoxide sensor 701 has higher sensitivity of detection, and the second carbon monoxide sensor 703 with lower sensitivity of detection. Namely, the first carbon monoxide sensor 701 measures low concentrations of carbon monoxide, while the second carbon monoxide sensor 703 measures high concentrations of carbon monoxide.

In this embodiment, the sensitivity of detection is controlled by taking advantage of the fact that the output voltage characteristics of carbon monoxide sensors differ by the catalysts used. The first carbon monoxide sensor 701 is the same as the carbon monoxide sensor 1 used in the first embodiment and includes platinum as electrode catalyst. The second carbon monoxide sensor 703, on the other hand, includes an alloy of platinum and ruthenium as electrode catalyst. The second carbon monoxide sensor 703 with the alloy catalyst has lower sensitivity of detection than that of the first carbon monoxide sensor 701 with the platinum catalyst.

Figure 14:
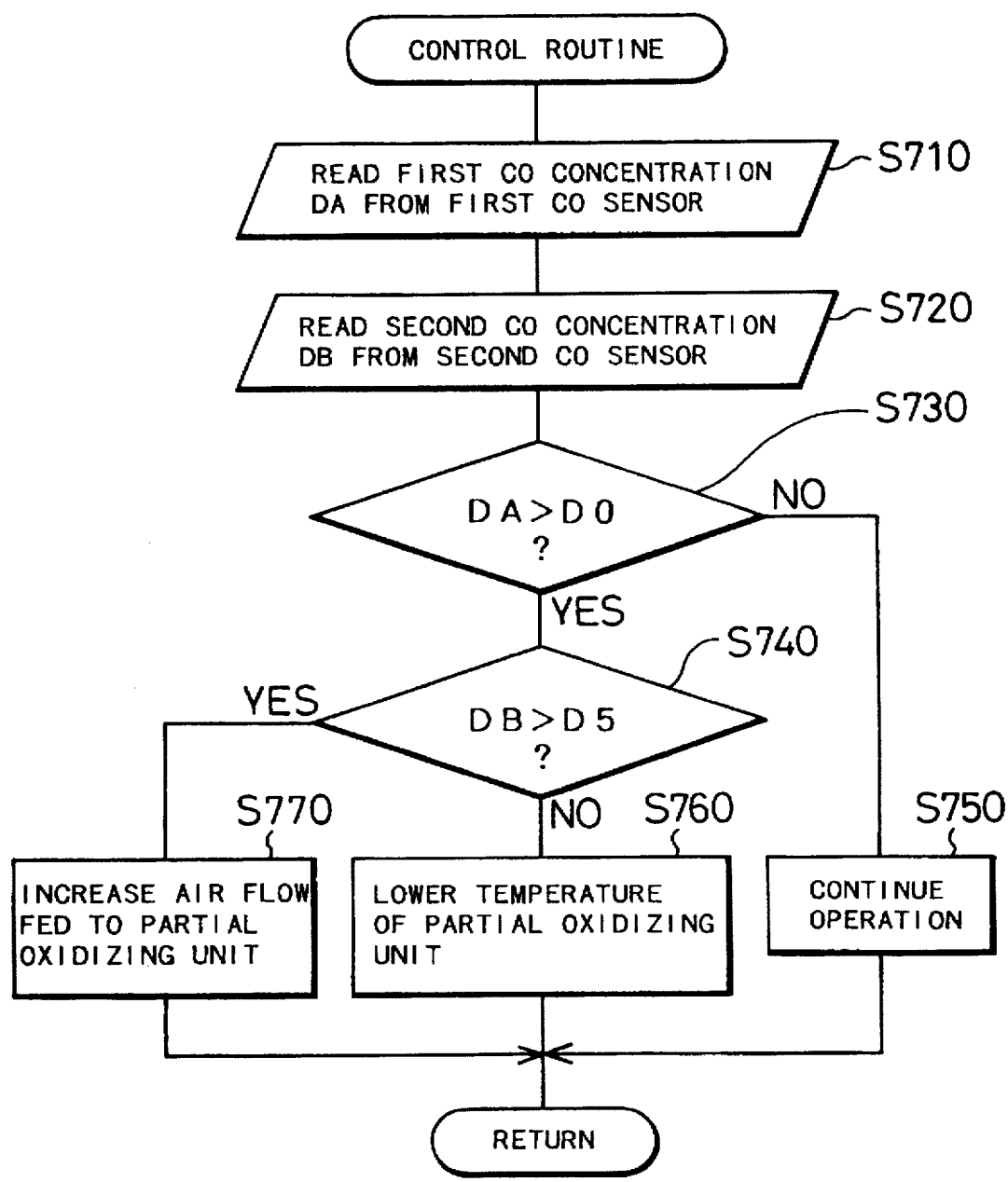
FIG. 14 is a flowchart showing a control routine executed by the CPU 232 of the electronic control unit 230 in the sixth embodiment.

The first and the second carbon monoxide sensor 701 and 703 are electrically connected to the electronic control unit 230. The electronic control unit 230 receives output signals from both the first and the second carbon monoxide sensors 701 and 703 and executes a required control process based on these output signals. FIG. 14 is a flowchart showing details of the control routine executed by the electronic control unit 230 in the sixth embodiment. The control routine of FIG. 14 is repeatedly executed at predetermined time intervals.

When the program enters the routine, the CPU 232 reads an output voltage of the first carbon monoxide sensor 701 to store the output voltage as a first carbon monoxide concentration DA at step S710. The CPU 232 then reads an output voltage of the second carbon monoxide sensor 703 to store the output voltage as a second carbon monoxide concentration DB at step S720.

The program then proceeds to step S730, at which the first carbon monoxide concentration DA input at step S710 is compared with a predetermined first level D0 (for example, 20 [ppm], equivalent to the predetermined level D0 used at step S260 in the flowchart of FIG. 5 of the first embodiment). At subsequent step S740, the second carbon monoxide concentration DB input at step S720 is compared with a predetermined second level D5 (for example, 50 [ppm]).

When the first carbon monoxide concentration DA is not greater than the predetermined first level D0 at step S730, the program goes to step S750 to continue operation of the fuel cell generator system 700 under the current operating conditions. In case that even the first carbon monoxide sensor 701 with higher sensitivity of detection can not measure the concentration of carbon monoxide, the CPU 232 is confident of normal operation of the fuel cell generator system 700 and continues the operation under the current conditions.

When the first carbon monoxide concentration DA is greater than the predetermined first level D0 at step S730 and the second carbon monoxide concentration DB is not greater than the predetermined second level D5 at step S740, the program proceeds to step S760. In this case, the concentration of carbon monoxide is measurable only by the first carbon monoxide sensor 701 with higher sensitivity of detection. The CPU 232 thus determines that an increase in concentration of carbon monoxide included in the gaseous fuel generated by the reformer 216 does not immediately affect the operation of the stack of fuel cells 210. At step S760, the CPU 232 accordingly controls the reformer 216 by a method of slower response to decrease the concentration of carbon monoxide. According to a concrete procedure, the CPU 232 lowers the temperature of the partial oxidizing unit 216c of the reformer 216 in the same manner as step S580 in the flowchart of FIG. 10 of the fourth embodiment.

When the first carbon monoxide concentration DA is greater than the predetermined first level D0 at step S730 and the second carbon monoxide concentration DB is greater than the predetermined second level D5 at step S740, the program proceeds to step S770. In this case, the concentration of carbon monoxide is measured by the second carbon monoxide sensor 703 with lower sensitivity of detection as well as the first carbon monoxide sensor 701 The CPU 232 thus determines that there is insufficient time to reduce the concentration of carbon monoxide. At step S770, the CPU 232 accordingly takes a measure of having an effect on the decrease in concentration of carbon monoxide with a quicker response. According to a concrete procedure, the CPU 232 increases the air flow fed to the partial oxidizing unit 216c of the reformer 216 in the same manner as step S590 in the flowchart of FIG. 10 of the fourth embodiment.

In the fuel cell generator system 700 of the sixth embodiment thus constructed, the use of two carbon monoxide sensors 701 and 703 with different sensitivities of detection favorably widens the detectable range of carbon monoxide. The structure of the sixth embodiment can accordingly detect an increase in concentration of carbon monoxide on the anode's side at its earlier stage, thereby preventing catalyst poisoning without delay and effectively canceling the catalyst poisoning.

In the sixth embodiment, even when both the first and the second carbon monoxide sensors 701 and 703 detect an increase in concentration of carbon monoxide, the CPU 232 does not suspend operation of the fuel cell generator system 700 but tries to decrease the concentration of carbon monoxide. In a preferable structure, however, when these conditions continue for a predetermined time period, the CPU 232 determines that there is no hope of recovery from catalyst poisoning and suspends operation of the fuel cell generator system 700 in the same manner as step S490 in the flowchart of FIG. 9 of the third embodiment.

Figure 15:
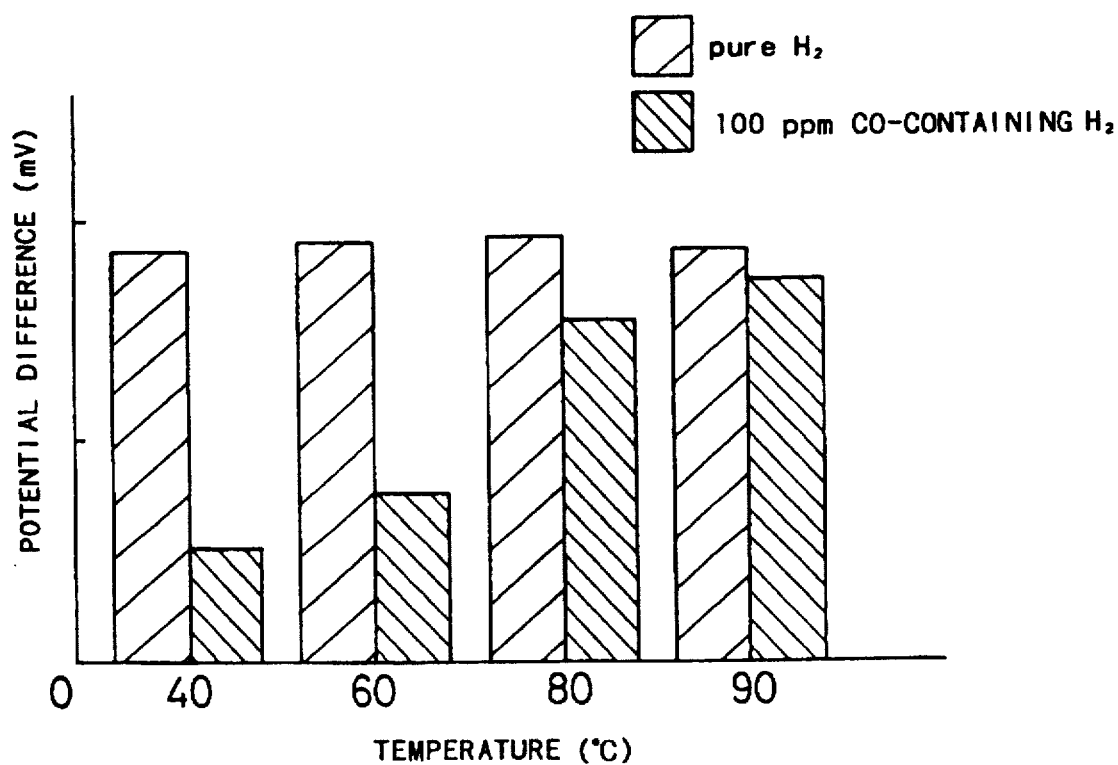
FIG. 15 is a graph showing a relationship between the temperature of the carbon monoxide sensor 1 and the potential difference.

In the sixth embodiment, the two carbon monoxide sensors used include different catalysts to have different sensitivities of detection. Alternatively, the sensitivity of detection may be controlled by taking advantage of the fact that the temperature of a carbon monoxide sensor varies its sensitivity of detection. Since the carbon monoxide sensors of the above embodiments have temperature dependence as described above, the sensitivity of detection can be controlled by heating or cooling the carbon monoxide sensor. FIG. 15 is a graph showing a relationship between the temperature of the carbon monoxide sensor 1 of the first embodiment and the output voltage (potential difference). This graph clearly shows that the potential difference is significantly varied by the temperature of the carbon monoxide sensor 1. A concrete structure of varying the temperature of a carbon monoxide sensor to control the sensitivity of detection is given below.

Figure 16:
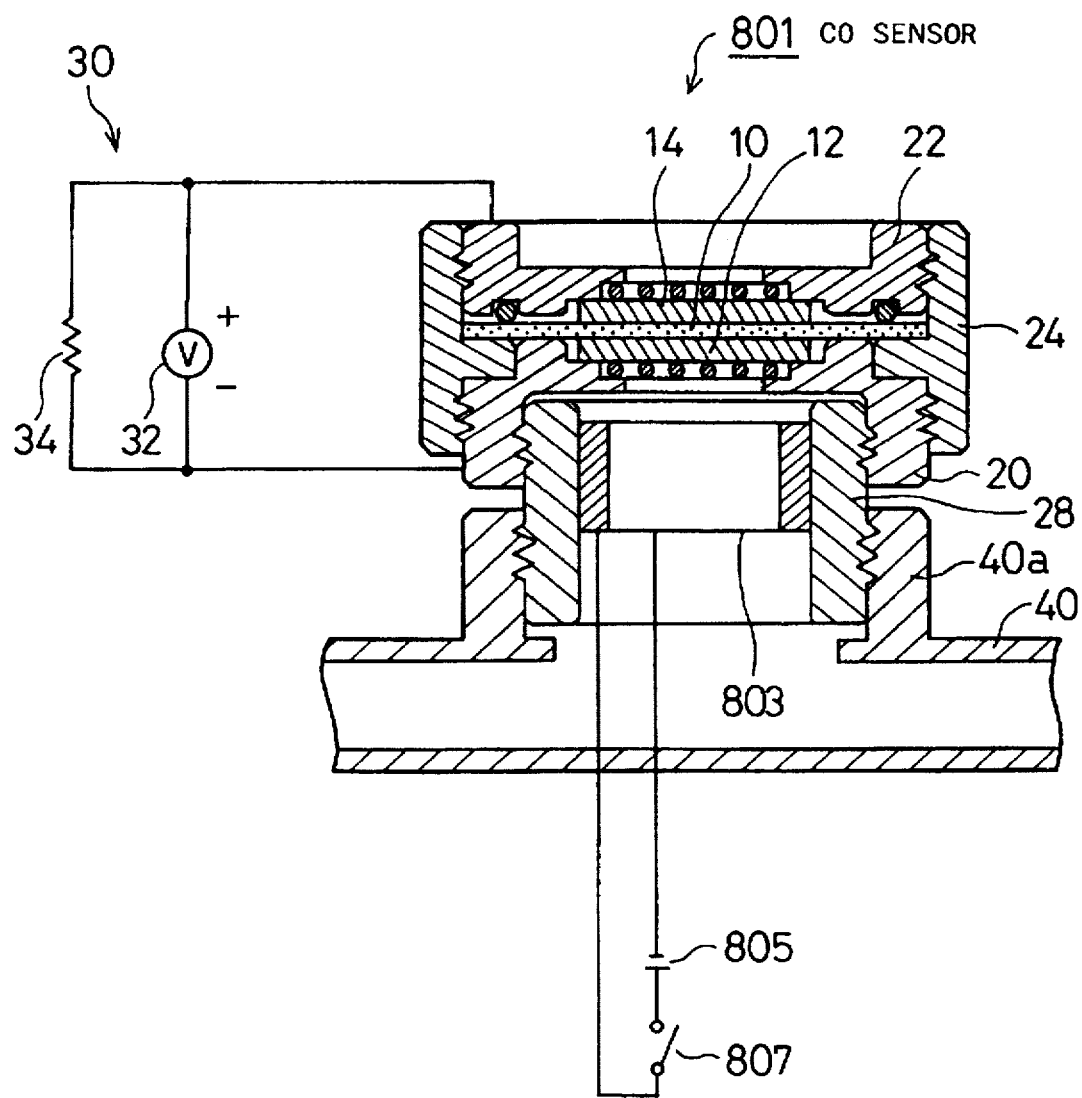
FIG. 16 is a vertical cross sectional view schematically illustrating structure of another carbon monoxide sensor 801 as a seventh embodiment according to the invention.

FIG. 16 is a vertical cross sectional view illustrating a carbon monoxide sensor 801 as a seventh embodiment according to the invention. The carbon monoxide sensor 801 has similar structure to that of the carbon monoxide sensor 1 of the first embodiment, except that a heater 803 is disposed in the gas flow conduit 28. The heater 803 is connected to a circuit including a secondary cell 805 and a switch 807. A control system (not shown) gives instructions to on and off the switch 807 and control the temperature of the carbon monoxide sensor 801, or at least the electrodes 12, to a preset level.

A cylindrical PTC heater is used for the heater 803 in this embodiment, although any other heating elements, such as nichrome wire and carbon-resistant heating elements, may also be applicable.

In the carbon monoxide sensor 801 thus constructed, the heater 803 raises the temperature of the carbon monoxide sensor 801, thereby enhancing the anti-poisoning properties of platinum catalyst. This structure including the heater 803 allows the sensitivity of detection to be set lower than that of the structure without any heater.

The carbon monoxide sensor 801 may be applied to the structure of the sixth embodiment described above. In such a case, the carbon monoxide sensor 801 is used as the second carbon monoxide sensor 703 with lower sensitivity of detection, whereas a carbon monoxide sensor without the heater 803 (for example, the carbon monoxide sensor 1 of the first embodiment) is used as the first carbon monoxide sensor 701 with higher sensitivity of detection. The temperature of the carbon monoxide sensor without a heater is substantially equal to the temperature of operation, which is approximately 80[° C.]. The preset level of temperature in the carbon monoxide sensor 801 with the heater 803 is accordingly controlled to be higher than 80° C. for the lower sensitivity of detection.

In the carbon monoxide sensor 801 of the seventh embodiment, an excessive increase in temperature of the electrode 12-electrolyte membrane 10-electrode 14 structure excessively dries the electrolyte membrane 10 and undesirably heightens the internal resistance. It is thus preferable that the preset level of temperature is controlled to be not higher than 100° C. Under the condition that the gaseous fuel on the anode's side is pressurized and sufficiently moistened, however, the electrolyte membrane 10 does not excessively dry even at temperatures of higher than 100° C. The preset level of temperature is thus controlled through the on-off operation of the heater 803 in an individual carbon monoxide sensor 801, according to the position of the carbon monoxide sensor 801, the required range of measurement of carbon monoxide concentration, and the temperature, pressure, humidity of the gaseous fuel fed to the anode.

Although the heater 803 is disposed on the side of the electrode 12 exposed to the gaseous fuel in the seventh embodiment, the heater may be arranged on the other side exposed to the atmosphere. Since the temperature of the gaseous fuel is generally higher than the temperature of the atmosphere, the arrangement of the heater 803 on the side of the electrode 14 exposed to the atmosphere requires a greater energy for maintaining the carbon monoxide sensor 801 at a constant temperature.

In the structure of the seventh embodiment, the sensitivity of detection of the carbon monoxide sensor 801 is lowered by raising the temperature of the carbon monoxide sensor 801 by means of the heater 803. The sensitivity of detection of the carbon monoxide sensor 801 can be heightened, on the contrary, by allowing part of coolant in the stack of fuel cells 210 to flow around the carbon monoxide sensor 801 so as to lower the temperature of the carbon monoxide sensor 801. In accordance with a concrete structure (not illustrated), a flow path is set in the insulating member 24 and part of coolant in the stack of fuel cells 210 is led into the flow path.

The carbon monoxide sensor 801 of temperature-decreasing structure may be applied to the sixth embodiment. In such a case, the carbon monoxide sensor 801 of this structure is used as the first carbon monoxide sensor 701 with higher sensitivity of detection.

A possible modification of the carbon monoxide sensor 801 is given below. The modification aims at effectively preventing the catalyst component on the electrode 12 exposed to the gaseous fuel from being critically poisoned by carbon monoxide of unexpectedly high concentration. The modified carbon monoxide sensor has substantially the same structure as that of the carbon monoxide sensor 801 of the seventh embodiment, except that the former sensor is set at higher temperatures of 140° C. through 160° C.

The heightened temperature of the carbon monoxide sensor to 140° C. through 160° C. allows the adsorbed carbon monoxide to be released from the surface of platinum catalyst on the electrode 12, thereby realizing recovery of catalytic activities. Heating by the heater 803 may continue for about one minute after the temperature of the carbon monoxide sensor is raised to 140° C. through 160° C.

In a fuel cell generator system including such a carbon monoxide sensor of modified structure, the heater 803 is activated at one or a combination of the following timings:

(1) at predetermined time intervals during the operation of the fuel cell generator system;

(2) at every activation of the fuel cell generator system;

(3) at every stop of the fuel cell generator system; and (4) at every time when the carbon monoxide sensor shows an extremely high concentration of carbon monoxide greater than a predetermined level.

In the carbon monoxide sensor of modified structure, the high temperature controlled by means of the heater 803 allows carbon monoxide adsorbed by the catalyst on the electrode 12 to be released, thereby attaining recovery of catalytic activities and preventing the performance of the carbon monoxide sensor from deteriorating.

Although the carbon monoxide sensors used in the above embodiments have an electrolyte membrane and a plurality of electrodes, any other structure may be applicable as long as it can measure the concentration of carbon monoxide included in the gaseous fuel.

The above embodiments are only illustrative and not restrictive in any sense. There may be many other modifications, alterations, and changes without departing from the scope or spirit of essential characteristics of the invention. The scope and spirit of the present invention are limited only by the terms of the appended claims.

What is claimed is:

1. A fuel cell generator comprising:

a reformer for reforming an original fuel to generate a hydrogen-containing gaseous fuel, a fuel cell comprising a pair of electrodes with a catalyst carried thereon, said fuel cell receiving said gaseous fuel fed to said electrodes thereof and generating an electromotive force through an electrochemical reaction of said gaseous fuel, carbon monoxide measurement means for measuring concentration of carbon monoxide included in said gaseous fuel;

reformer operation control means for controlling operation of said reformer according to the concentration of carbon monoxide measured by said carbon monoxide measurement means, to decrease the concentration of carbon monoxide included in said gaseous fuel, a first flow path for supplying said gaseous fuel to said fuel cell, a second flow path for discharging a residual gas of said gaseous fuel from said fuel cell; and wherein said carbon monoxide measurement means comprises:

a carbon monoxide sensor disposed in said second flow path.

2. A fuel cell generator in accordance with claim 1, wherein said carbon monoxide measurement means additionally comprises:

a carbon monoxide sensor disposed in said first flow path.

3. A fuel cell generator comprising:

a reformer for reforming an original fuel to generate a hydrogen-containing gaseous fuel, a fuel cell comprising a pair of electrodes with a catalyst carried thereon, said fuel cell receiving said gaseous fuel fed to said electrodes thereof and generating an electromotive force through an electrochemical reaction of said gaseous fuel, carbon monoxide measurement means for measuring concentration of carbon monoxide included in said gaseous fuel; and reformer operation control means for controlling operation of said reformer according to the concentration of carbon monoxide measured by said carbon monoxide measurement means, to decrease the concentration of carbon monoxide included in said gaseous fuel, wherein said carbon monoxide measurement means comprises:

a first carbon monoxide sensor having a first sensitivity of detection; and a second carbon monoxide sensor having a second sensitivity of detection, which is different from said first sensitivity of detection.

4. A fuel cell generator in accordance with claim 3, wherein each of said first carbon monoxide sensor and said second carbon monoxide sensor comprises:

an electrolyte membrane;

first and second electrodes with a catalyst carried thereon, said first and second electrodes being arranged across said electrolyte membrane;

a gaseous fuel supply conduit for supplying said gaseous fuel to said first electrode;

an oxygen gas supply conduit for supplying an oxygen-containing gas to said second electrode; and potential difference detection means for measuring a potential difference between said first and second electrodes while a preset load is connected to said first and second electrodes; and wherein said first carbon monoxide sensor includes platinum as said catalyst, and said second carbon monoxide sensor includes a platinum-containing alloy as said catalyst.

5. A fuel cell generator in accordance with claim 3, wherein each of said first carbon monoxide sensor and said second carbon monoxide sensor comprises:

an electrolyte membrane;

first and second electrodes with a catalyst carried thereon, said first and second electrodes being arranged across said electrolyte membrane;

a gaseous fuel supply conduit for supplying said gaseous fuel to said first electrode;

an oxygen gas supply conduit for supplying an oxygen-containing gas to said second electrode; and potential difference detection means for measuring a potential difference between said first and second electrodes while a preset load is connected to said first and second electrodes; and wherein either one of said first carbon monoxide sensor and said second carbon monoxide sensor further comprises temperature control means for controlling temperature of said first electrode.

6. A fuel cell generator comprising:

a reformer for reforming an original fuel to generate a hydrogen-containing gaseous fuel, a fuel cell comprising a pair of electrodes with a catalyst carried thereon, said fuel cell receiving said gaseous fuel fed to said electrodes thereof and generating an electromotive force through an electrochemical reaction of said gaseous fuel, carbon monoxide measurement means for measuring concentration of carbon monoxide included in said gaseous fuel; and reformer operation control means for controlling operation of said reformer according to the concentration of carbon monoxide measured by said carbon monoxide measurement means, to decrease the concentration of carbon monoxide included in said gaseous fuel, wherein said reformer comprises:

a reformer unit for converting methanol and water to a reformed gas containing hydrogen and carbon dioxide;

a partial oxidizing unit for oxidizing carbon monoxide generated as a by-product of said reformed gas, and said reformer operation control means further comprises:

partial oxidizing unit control means for comparing the concentration of carbon monoxide measured by said carbon monoxide measurement means with a first preset value, and increasing an air flow fed to said partial oxidizing unit when the measured concentration of carbon monoxide is greater than said first preset value.

7. A fuel cell generator in accordance with claim 6, further comprising:

a first flow path for supplying said gaseous fuel to said fuel cell; and a second flow path for discharging a residual gas of said gaseous fuel from said fuel cell; and wherein said carbon monoxide measurement means comprises:

a first carbon monoxide sensor disposed in said first flow path, for generating a first output representing the concentration of carbon monoxide, said first output being compared with said first preset value by said partial oxidizing unit control means; and a second carbon monoxide sensor disposed in said second flow path, for generating a second output representing the concentration of carbon monoxide; and wherein said fuel cell generator further comprising:

means for suspending operation of said fuel cell when said first output is greater than said first preset value and said second output is greater than a second preset value, which is greater than said first preset value.

8. A fuel cell generator comprising:

a reformer for reforming an original fuel to generate a hydrogen-containing gaseous fuel, a fuel cell comprising a pair of electrodes with a catalyst carried thereon said fuel cell receiving said gaseous fuel fed to said electrodes thereof and generating an electromotive force through an electrochemical reaction of said gaseous fuel, carbon monoxide measurement means for measuring concentration of carbon monoxide included in said gaseous fuel; and reformer operation control means for controlling operation of said reformer according to the concentration of carbon monoxide measured by said carbon monoxide measurement means to decrease the concentration of carbon monoxide included in said gaseous fuel, said fuel cell generator further comprising:

gas utilization calculation means for calculating a degree of utilization of said gaseous fuel in said fuel cell as a gas utilization rate; and gas utilization rate decreasing means for inactivating said reformer operation control means and controlling operation of said reformer to decrease the gas utilization rate when said gas utilization rate is greater than a preset level.

9. A fuel cell generator comprising:

a reformer for reforming an original fuel to generate a hydrogen-containing gaseous fuel, a fuel cell comprising a pair of electrodes with a catalyst carried thereon, said fuel cell receiving said gaseous fuel fed to said electrodes thereof and generating an electromotive force through an electrochemical reaction of said gaseous fuel, carbon monoxide measurement means for measuring concentration of carbon monoxide included in said gaseous fuel; and reformer operation control means for controlling operation of said reformer according to the concentration of carbon monoxide measured by said carbon monoxide measurement means, to decrease the concentration of carbon monoxide included in said gaseous fuel, wherein said carbon monoxide measurement means comprises:

an electrolyte membrane;

first and second electrodes with a catalyst carried thereon, said first and second electrodes being arranged across said electrolyte membrane;

a gaseous fuel supply conduit for supplying said gaseous fuel to said first electrode;

an oxygen gas supply conduit for supplying an oxygen-containing gas to said second electrode; and potential difference detection means for measuring a potential difference between said first and second electrodes while a preset load is connected to said first and second electrodes.

10. A method of generating an electromotive force with a fuel cell comprising a pair of electrodes with a catalyst carried thereon, said method comprising the steps of:

(a) reforming an original fuel to generate a hydrogen-containing gaseous fuel;

(b) feeding said gaseous fuel to the electrodes of said fuel cell;

(c) measuring concentration of carbon monoxide included in said gaseous fuel; and (d) controlling generation of said gaseous fuel in said step (a) according to the concentration of carbon monoxide measured in said step (c), to decrease the concentration of carbon monoxide included in said gaseous fuel, wherein said step (c) comprises the steps of:

(c-1) measuring concentration of carbon monoxide included in said gaseous fuel before said gaseous fuel is fed to said fuel cell; and (c-2) measuring concentration of carbon monoxide included in said gaseous fuel discharged from said fuel cell.

11. A method of generating an electromotive force with a fuel cell comprising a pair of electrodes with a catalyst carried thereon, said method comprising the steps of:

(a) reforming an original fuel to generate a hydrogen-containing gaseous fuel;

(b) feeding said gaseous fuel to the electrodes of said fuel cell;

(c) measuring concentration of carbon monoxide included in said gaseous fuel; and (d) controlling generation of said gaseous fuel in said step (a) according to the concentration of carbon monoxide measured in said step (c), to decrease the concentration of carbon monoxide included in said gaseous fuel, wherein said step (c) comprises the steps of:

(c-3) detecting carbon monoxide with a first sensitivity of detection; and (c-4) detecting carbon monoxide with a second sensitivity of detection, which is different from said first sensitivity of detection.

12. A method in accordance with claim 11, wherein each of said step (c-3) and said step (c-4) further comprises the steps of:

(c-5) supplying said gaseous fuel to a first electrode, which is one of two electrodes having a catalyst carried thereon and being arranged across an electrolyte membrane;

(c-6) supplying an oxygen-containing oxidizing gas to a second electrode, which is the other of said two electrodes; and (c-7) measuring a potential difference between said first and second electrodes while a preset load is connected to said first and second electrodes; and wherein either one of said step (c-3) and said step (c-4) further comprising the step of:

(c-8) controlling temperature of said first electrode.

13. A method of generating an electromotive force with a fuel cell comprising a pair of electrodes with a catalyst carried thereon, said method comprising the steps of:

(a) reforming an original fuel to generate a hydrogen-containing gaseous fuel;

(b) feeding said gaseous fuel to the electrodes of said fuel cell;

(c) measuring concentration of carbon monoxide included in said gaseous fuel; and (d) controlling generation of said gaseous fuel in said step (a) according to the concentration of carbon monoxide measured in said step (c), to decrease the concentration of carbon monoxide included in said gaseous fuel, wherein said step (a) comprises the steps of:
  (a-1) converting methanol and water to a reformed gas containing hydrogen and carbon dioxide; and
  (a-2) oxidizing carbon monoxide generated as a by-product of said reformed gas, said step (d) further comprises the steps of:
  (d-1) comparing the concentration of carbon monoxide measured in said step (c) with a first preset value, and increasing an air flow used in said step (a-2) when the measured concentration of carbon monoxide is greater than said first preset value.

14. A method in accordance with claim 13, wherein said step (c) further comprises the steps of:
  (c-9) measuring concentration of carbon monoxide included in said gaseous fuel before said gaseous fuel being fed to said fuel cell; said concentration of carbon monoxide being compared with said first preset value in said step (d-1); and
  (c-10) measuring concentration of carbon monoxide included in said gaseous fuel discharged from said fuel cell, said method further comprising the step of:
  (e) suspending operation of said fuel cell when the concentration of carbon monoxide measured in said step (c-9) is greater than said first preset value and the concentration of carbon monoxide measured in said step (c-10) is greater than a second preset value, which is greater than said first preset value.

15. A method of generating an electromotive force with a fuel cell comprising a pair of electrodes with a catalyst carried thereon, said method comprising the steps of:
  (a) reforming an original fuel to generate a hydrogen-containing gaseous fuel;
  (b) feeding said gaseous fuel to the electrodes of said fuel cell;
  (c) measuring concentration of carbon monoxide included in said gaseous fuel; and
  (d) controlling generation of said gaseous fuel in said step (a) according to the concentration of carbon monoxide measured in said step (c), to decrease the concentration of carbon monoxide included in said gaseous fuel, said method further comprising the steps of:
  (f) calculating a degree of utilization of said gaseous fuel in said fuel cell as a gas utilization rate; and
  (g) interfering with control in said step (d) and controlling generation of said gaseous fuel in said step (a) to decrease the gas utilization rate when the gas utilization rate calculated in said step (f) is greater than a preset level.

16. A method of generating an electromotive force with a fuel cell comprising a pair of electrodes with a catalyst carried thereon, said method comprising the steps of:
  (a) reforming an original fuel to generate a hydrogen-containing gaseous fuel;
  (b) feeding said gaseous fuel to the electrodes of said fuel cell;
  (c) measuring concentration of carbon monoxide included in said gaseous fuel; and
  (d) controlling generation of said gaseous fuel in said step (a) according to the concentration of carbon monoxide measured in said step (c), to decrease the concentration of carbon monoxide included in said gaseous fuel, wherein said step (c) comprises the steps of:
  (c-11) supplying said gaseous fuel to a first electrode, which is one of two electrodes having a catalyst carried thereon and being arranged across an electrolyte membrane;
  (c-12) supplying an oxygen-containing oxidizing gas to a second electrode, which is the other of said two electrodes; and
  (c-13) measuring a potential difference between said first and second electrodes while a preset load is connected to said first and second electrodes.

* * * * *